US008916358B2

(12) United States Patent
Swartz

(10) Patent No.: US 8,916,358 B2
(45) Date of Patent: Dec. 23, 2014

(54) METHODS FOR CONTROL OF FLUX IN METABOLIC PATHWAYS THROUGH PROTEASE MANIPULATION

(75) Inventor: James R. Swartz, Menlo Park, CA (US)

(73) Assignees: GreenLight Biosciences, Inc., Medford, MA (US); The Board of Trustees of the Leland Stanford Junior University, Palo Alto, CA (US)

( * ) Notice: Subject to any disclaimer, the term of this patent is extended or adjusted under 35 U.S.C. 154(b) by 311 days.

(21) Appl. No.: 13/223,042

(22) Filed: Aug. 31, 2011

(65) Prior Publication Data
US 2012/0052547 A1 Mar. 1, 2012

Related U.S. Application Data

(60) Provisional application No. 61/378,828, filed on Aug. 31, 2010.

(51) Int. Cl.
C12P 1/00 (2006.01)
C12P 19/30 (2006.01)
C12N 9/50 (2006.01)
C12N 15/52 (2006.01)
C12P 7/42 (2006.01)

(52) U.S. Cl.
CPC ............. *C12P 19/305* (2013.01); *C12N 9/50* (2013.01); *C12N 15/52* (2013.01); *C12P 7/42* (2013.01)
USPC .......................................................... 435/41

(58) Field of Classification Search
None
See application file for complete search history.

(56) References Cited

U.S. PATENT DOCUMENTS

| | | |
|---|---|---|
| 3,684,652 A | 8/1972 | Nakayama et al. |
| 3,950,357 A | 4/1976 | Kahan et al. |
| RE28,886 E | 6/1976 | Nakayama et al. |
| 4,006,060 A | 2/1977 | Kahan et al. |
| 4,194,047 A | 3/1980 | Christensen et al. |
| 4,270,537 A | 6/1981 | Romaine |
| 4,292,436 A | 9/1981 | Liu et al. |
| 4,329,481 A | 5/1982 | Liu et al. |
| 4,374,772 A | 2/1983 | Hazen et al. |
| 4,438,201 A | 3/1984 | Kubo et al. |
| 4,458,066 A | 7/1984 | Caruthers et al. |
| 4,460,689 A | 7/1984 | Foor et al. |
| 4,596,556 A | 6/1986 | Morrow et al. |
| 4,790,824 A | 12/1988 | Morrow et al. |
| 4,886,499 A | 12/1989 | Cirelli et al. |
| 4,940,460 A | 7/1990 | Casey et al. |
| 4,941,880 A | 7/1990 | Burns |
| 4,946,783 A | 8/1990 | Beckwith et al. |
| 4,950,603 A | 8/1990 | Ingolia et al. |
| 5,001,055 A | 3/1991 | Imahori et al. |
| 5,015,235 A | 5/1991 | Crossman |
| 5,064,413 A | 11/1991 | McKinnon et al. |
| 5,070,020 A | 12/1991 | Ingolia et al. |
| 5,141,496 A | 8/1992 | Dalto et al. |
| 5,190,521 A | 3/1993 | Hubbard et al. |
| 5,312,335 A | 5/1994 | McKinnon et al. |
| 5,319,122 A | 6/1994 | Friedman |
| 5,328,483 A | 7/1994 | Jacoby |
| 5,334,144 A | 8/1994 | Alchas et al. |
| 5,339,163 A | 8/1994 | Homma et al. |
| 5,383,851 A | 1/1995 | McKinnon et al. |
| 5,417,662 A | 5/1995 | Hjertman et al. |
| 5,436,131 A | 7/1995 | Condra et al. |
| 5,466,220 A | 11/1995 | Brenneman |
| 5,480,381 A | 1/1996 | Weston |
| 5,503,627 A | 4/1996 | McKinnon et al. |
| 5,520,639 A | 5/1996 | Peterson et al. |
| 5,527,288 A | 6/1996 | Gross et al. |
| 5,569,189 A | 10/1996 | Parsons |
| 5,593,856 A | 1/1997 | Choi et al. |
| 5,599,302 A | 2/1997 | Lilley et al. |
| 5,649,912 A | 7/1997 | Peterson |
| 5,672,497 A | 9/1997 | Cox et al. |
| 5,704,911 A | 1/1998 | Parsons |
| 5,871,922 A | 2/1999 | Salmond et al. |
| 5,893,397 A | 4/1999 | Peterson et al. |
| 5,993,412 A | 11/1999 | Deily et al. |
| 6,168,931 B1 | 1/2001 | Swartz et al. |
| 6,387,667 B1 | 5/2002 | Maruyama et al. |

(Continued)

FOREIGN PATENT DOCUMENTS

| | | |
|---|---|---|
| EP | 0377295 A1 | 7/1990 |
| EP | 0444775 A1 | 9/1991 |

(Continued)

OTHER PUBLICATIONS

Collins-Racie et al., Production of recombinant bovine enterokinase catalytic subunit in *Escherichia coli* using the novel secretory fusion partner DsbA. Biotechnology (N Y). Sep. 1995;13(9):982-7.
Invitation to Pay Additional Fees for PCT/US2011/035639 mailed Sep. 12, 2011.
International Search Report and Written Opinion for PCT/US2011/035639 mailed Nov. 18, 2011.
International Search Report and Written Opinion for PCT/US2009/067841mailed Mar. 22, 2010.
International Preliminary Report on Patentability for PCT/US2009/067841 mailed Jun. 21, 2011.
International Search Report and Written Opinion for PCT/US2009/006704 mailed Mar. 3, 2010.

(Continued)

*Primary Examiner* — Sheridan Swope
(74) *Attorney, Agent, or Firm* — Wolf, Greenfield & Sacks, P.C.; C. Hunter Baker; Heather J. DiPietrantonio

(57) ABSTRACT

The embodiments described herein pertain to cells, and methods for preparing cells, that can be used as biocatalysts by altering enzymes that compete for a substrate or product of a pathway of interest such that the targeted enzyme is sensitive to a site-specific protease, which protease is expressed but relocated in the cell to a site where it is not in contact with the targeted enzyme in the intact cell. Upon cell lysis, the protease contacts the target enzyme, which is then inactivated by protease cleavage.

24 Claims, 1 Drawing Sheet

(56) References Cited

U.S. PATENT DOCUMENTS

| | | | |
|---|---|---|---|
| 6,440,688 | B1 | 8/2002 | Bruce et al. |
| 6,472,169 | B1 | 10/2002 | Frost et al. |
| 6,531,299 | B1 | 3/2003 | Khosla et al. |
| 6,746,859 | B1 | 6/2004 | LaVallie |
| 6,921,659 | B2 | 7/2005 | Joly |
| 6,994,986 | B2 | 2/2006 | Swartz et al. |
| 7,041,479 | B2 | 5/2006 | Swartz et al. |
| 7,223,390 | B2 | 5/2007 | Brown |
| 7,226,767 | B2 | 6/2007 | Maruyama et al. |
| 7,312,049 | B2 | 12/2007 | Calhoun et al. |
| 7,338,789 | B2 | 3/2008 | Swartz et al. |
| 7,341,852 | B2 | 3/2008 | Voloshin et al. |
| 7,351,563 | B2 | 4/2008 | Swartz et al. |
| 2002/0058303 | A1 | 5/2002 | Swartz et al. |
| 2002/0127633 | A1 | 9/2002 | Dilley et al. |
| 2003/0022178 | A1 | 1/2003 | Schneewind et al. |
| 2003/0113778 | A1 | 6/2003 | Schulte et al. |
| 2004/0002103 | A1 | 1/2004 | Short |
| 2004/0038250 | A1 | 2/2004 | Nunez et al. |
| 2004/0209321 | A1 | 10/2004 | Swartz et al. |
| 2005/0054044 | A1 | 3/2005 | Swartz et al. |
| 2006/0281148 | A1 | 12/2006 | Swartz et al. |
| 2007/0111283 | A1 | 5/2007 | Cannon et al. |
| 2007/0154983 | A1 | 7/2007 | Calhoun et al. |
| 2007/0202198 | A1 | 8/2007 | Purcell |
| 2008/0131925 | A1 | 6/2008 | Berk et al. |
| 2009/0124012 | A1 | 5/2009 | Nikolsky et al. |
| 2009/0275096 | A1 | 11/2009 | Burgard et al. |
| 2009/0312539 | A1 | 12/2009 | Gnanaprakasam et al. |
| 2010/0291653 | A1 | 11/2010 | Ness et al. |
| 2011/0008867 | A1 | 1/2011 | Zarur et al. |
| 2011/0099670 | A1 | 4/2011 | Koops et al. |
| 2011/0269198 | A1 | 11/2011 | Klein-Marcuschamer |
| 2011/0275116 | A1 | 11/2011 | Swartz |
| 2012/0052547 | A1 | 3/2012 | Swartz |
| 2012/0070870 | A1 | 3/2012 | Way et al. |
| 2013/0065878 | A1 | 3/2013 | Blake et al. |

FOREIGN PATENT DOCUMENTS

| | | |
|---|---|---|
| EP | 0553821 A1 | 8/1993 |
| EP | 1 433 856 A1 | 6/2004 |
| EP | 1502956 A1 | 2/2005 |
| EP | 1939210 A1 | 7/2008 |
| EP | 2204453 A1 | 7/2010 |
| GB | 2 018 822 A | 10/1979 |
| WO | WO 97/13537 A1 | 4/1997 |
| WO | WO 97/37705 A1 | 10/1997 |
| WO | WO 98/07690 A1 | 2/1998 |
| WO | WO 99/34850 A1 | 7/1999 |
| WO | WO 00/03581 A1 | 1/2000 |
| WO | WO 00/55353 A1 | 9/2000 |
| WO | WO 2005/098048 A1 | 10/2005 |
| WO | WO 2007/053655 A2 | 5/2007 |
| WO | WO 2007/137144 A2 | 11/2007 |
| WO | WO 2008/002661 A2 | 1/2008 |
| WO | WO 2008/002663 A2 | 1/2008 |
| WO | WO 2008/002673 A2 | 1/2008 |
| WO | WO 2008/066583 A2 | 6/2008 |
| WO | WO 2008/088884 A2 | 7/2008 |
| WO | WO 2008/094546 A2 | 8/2008 |
| WO | WO 2010/046713 A2 | 4/2010 |
| WO | WO 2010/074760 A1 | 7/2010 |
| WO | WO 2010/077806 A1 | 7/2010 |
| WO | WO 2011/017560 A1 | 2/2011 |
| WO | WO 2011/072287 A2 | 6/2011 |
| WO | WO 2011/140516 A2 | 11/2011 |
| WO | WO 2012/030980 A1 | 3/2012 |

OTHER PUBLICATIONS

International Preliminary Report on Patentability for PCT/US2009/006704 mailed Jul. 7, 2011.

[No Author Listed] Biolistic® Particle Delivery System Bibliography. Bio-Rad Technical Bulletin #1687. Bio-Rad Laboratories. 12 pages.

[No Author Listed] Biapenem. Drugs Fut. 1994;19(7):631-637.

Adams et al., Hindered dialkylamino nucleoside phosphite reagents in the synthesis of two DNA 51-mers. J Am Chem Soc. 1983;105(3):661-3.

Alber et al., Malonyl-coenzyme A reductase in the modified 3-hydroxypropionate cycle for autotrophic carbon fixation in archaeal *Metallosphaera* and *Sulfolobus* spp. J Bacteriol. Dec. 2006;188(24):8551-9. Epub Oct. 13, 2006.

Allain, Cell-free ethanol production: the future of fuel ethanol? J Chem Technol Biotechnol. 2007;82:117-20.

Alper et al., Tuning genetic control through promoter engineering. Proc Natl Acad Sci U S A. Sep. 6, 2005;102(36):12678-83. Epub Aug. 25, 2005.

Alves-Pereira et al., CDP-alcohol hydrolase, a very efficient activity of the 5'-nucleotidase/udp-sugar hydrolase encoded by the usha gene of *Yersinia intermedia* and *Escherichia coli*. J Bacteriol. Sep. 15, 2008;190(18):6153-61. Published ahead of print Jul. 18, 2008, doi:10.1128/JB.00658-08.

Anthony et al., Optimization of the mevalonate-based isoprenoid biosynthetic pathway in *Escherichia coli* for production of the antimalarial drug precursor amorpha-4,11-diene. Metab Eng. Jan. 2009;11(1):13-9. Epub Aug. 12, 2008.

Atsumi et al., Metabolic engineering of *Escherichia coli* for 1-butanol production. Metab Eng. Nov. 2008;10(6):305-11. Epub Sep. 14, 2007.

Atsumi et al., Non-fermentative pathways for synthesis of branched-chain higher alcohols as biofuels. Nature. Jan. 3, 2008;451(7174):86-9.

Bateson et al., Olivanic acid analogues. Part 6. Biomimetic synthesis of (±)-PS-5, (±)-6-Epi-PS-5, and (±)-benzyl MM22381. J Chem Soc Perkin Trans 1. 1990;1793-1801.

Baum et al., Beta-Galactosidase containing a human immunodeficiency virus protease cleavage site is cleaved and inactivated by human immunodeficiency virus protease. Proc Natl Acad Sci U S A. Dec. 1990;87(24):10023-7.

Beaucage et al., Deoxynucleoside phosphoramidites—A new class of key intermediates for deoxypolynucleotide synthesis. Tetra Lett. 1981;22(20):1859-62.

Belousov et al., Sequence-specific targeting and covalent modification of human genomic DNA. Nucleic Acids Res. Sep. 1, 1997;25(17):3440-4.

Benton et al., Screening lambdagt recombinant clones by hybridization to single plaques in situ. Science. Apr. 8, 1977;196(4286):180-2.

Berge et al., Pharmaceutical salts. J Pharmaceut Sci. Jan. 1977;66(1):1-19.

Blommers et al., Effects of the introduction of L-nucleotides into DNA. Solution structure of the heterochiral duplex d(G-C-G-(L)T-G-C-G).d(C-G-C-A-C-G-C) studied by NMR spectroscopy. Biochemistry. Jun. 28, 1994;33(25):7886-96.

Bodner et al., Non-heme iron oxygenases generate natural structural diversity in carbapenem antibiotics. J Am Chem Soc. Jan. 13, 2010;132(1):12-3.

Boiteux et al., Design of glycolysis. Philos Trans R Soc Lond B Biol Sci. Jun. 26, 1981;293(1063):5-22.

Bongaerts et al., Metabolic engineering for microbial production of aromatic amino acids and derived compounds. Metab Eng. Oct. 2001;3(4):289-300.

Boyer et al., Cell-free synthesis and maturation of [FeFe] hydrogenases. Biotechnol Bioeng. Jan. 1, 2008;99(1):59-67.

Bradley, Star role for bacteria in controlling flu pandemic? Nat Rev Drug Discov. Dec. 2005;4(12):945-6.

Brown et al., Chemical synthesis and cloning of a tyrosine tRNA gene. Methods Enzymol. 1979;68:109-51.

Buist et al., Different subcellular locations of secretome components of Gram-positive bacteria. Microbiology. Oct. 2006;152(Pt 10):2867-74.

Calhoun et al., An economical method for cell-free protein synthesis using glucose and nucleoside monophosphates. Biotechnol Prog. Jul.-Aug. 2005;21(4):1146-53.

(56) References Cited

OTHER PUBLICATIONS

Calhoun et al., Energizing cell-free protein synthesis with glucose metabolism. Biotechnol Bioeng. Jun. 5, 2005;90(5):606-13.
Calhoun et al., Energy systems for ATP regeneration in cell-free protein synthesis reactions. Methods in Molecular Biology. In vitro transcription and translation protocols. 375(2):3-17.
Calhoun et al., Total amino acid stabilization during cell-free protein synthesis reactions. J Biotechnol. May 17, 2006;123(2):193-203. Epub Jan. 26, 2006.
Campbell et al., The CTP:phosphocholine cytidylyltransferase encoded by the licC gene of *Streptococcus pneumoniae*: cloning, expression, purification, and characterization. Biochim Biophys Acta. Dec. 30, 2001;1534(2-3):85-95.
Chandran et al., Phosphoenolpyruvate availability and the biosynthesis of shilcimic acid. Biotechnol Prog. May-Jun. 2003;19(3):808-14.
Chang et al., YPA: an integrated repository of promoter features in *Saccharomyces cerevisiae*. Nucleic Acids Res. Jan. 2011;39(Database issue):D647-52. Epub Nov. 2, 2010.
Chen et al., A modified osmotic shock for periplasmic release of a recombinant creatinase from *Escherichia coli*. Biochem Eng J. 2004;19:211-5.
Chen et al., Crystal structures of penicillin-binding protein 6 from *Escherichia coli*. J Am Chem Soc. Oct. 14, 2009;131(40):14345-54.
Chen et al., High-level accumulation of a recombinant antibody fragment in the periplasm of *Escherichia coli* requires a triple-mutant (degP prc spr) host strain. Biotechnol Bioeng. Mar. 5, 2004;85(5):463-74.
Chiu et al., Site-directed, Ligase-Independent Mutagenesis (SLIM): a single-tube methodology approaching 100% efficiency in 4 h. Nucleic Acids Res. Dec. 7, 2004;32(21):e174.
Chong et al., Single-column purification of free recombinant proteins using a self-cleavable affinity tag derived from a protein splicing element. Gene. Jun. 19, 1997;192(2):271-81.
Choubey et al., Molecular characterization and localization of *Plasmodium falciparum* choline kinase. Biochim Biophys Acta. Jul. 2006;1760(7):1027-38.
Coulthurst et al., Regulation and biosynthesis of carbapenem antibiotics in bacteria. Nat Rev Microbiol. Apr. 2005;3(4):295-306. *Erratum* included.
Dahiyat et al., De novo protein design: fully automated sequence selection. Science. Oct. 3, 1997;278(5335):82-7.
Dahl et al., Isolation and characterization of Chinese hamster ovary cells defective in the intracellular metabolism of low density lipoprotein-derived cholesterol. J Biol Chem. Mar. 5, 1992;267(7):4889-96.
Dani et al., Isolation and characterization of a thylakoid membrane module showing partial light and dark reactions. Biochim Biophys Acta. May 15, 2005;1669(1):43-52.
Daniell et al., Transformation of the cyanobacterium Anacystis nidulans 6301 with the *Escherichia coli* plasmid pBR322. Proc Natl Acad Sci U S A. Apr. 1986;83(8):2546-50.
Datsenko et al., One-step inactivation of chromosomal genes in *Escherichia coli* K-12 using PCR products. Proc Natl Acad Sci U S A. Jun. 6, 2000;97(12):6640-5.
De Boer et al., Protein targeting towards the thylakoid lumen of chloroplasts: proper localization of fusion proteins is only observed in vivo. EMBO J. Oct. 1991;10(10):2765-72.
De Mey et al., Construction and model-based analysis of a promoter library for *E. coli*: an indispensable tool for metabolic engineering. BMC Biotechnol. Jun. 18, 2007;7:34.
Dietrich et al., A novel semi-biosynthetic route for artemisinin production using engineered substrate-promiscuous P450(BM3). ACS Chem Biol. Apr. 17, 2009;4(4):261-7.
Dingwall et al., The nucleoplasmin nuclear location sequence is larger and more complex than that of SV-40 large T antigen. J Cell Biol. Sep. 1988;107(3):841-9.
Draper et al., Ti plasmid homologous sequences present in tissues from agrobacterium plasmid-transformed petunia protoplasts. Plant Cell Physiol. 1982;23(3):451-8.

Elander, Industrial production of beta-lactam antibiotics. Appl Microbiol Biotechnol. Jun. 2003;61(5-6):385-92. Epub Apr. 3, 2003.
Erb et al., Carboxylation mechanism and stereochemistry of crotonyl-CoA carboxylase/reductase, a carboxylating enoyl-thioester reductase. Proc Natl Acad Sci U S A. Jun. 2, 2009;106(22):8871-6. Epub May 20, 2009.
Erb et al., Synthesis of C5-dicarboxylic acids from C2-units involving crotonyl-CoA carboxylase/reductase: The ethylmalonyl-CoA pathway. Proc Nat Acad Sci. Jun. 4, 2007;104(25):10631-6.
Evans et al., The asymmetric synthesis of β-lactam antibiotics—IV. A formal synthesis of thienamycin. Tetra Lett. 1986;27(41):4961-4.
Flores et al., Pathway engineering for the production of aromatic compounds in *Escherichia coli*. Nat Biotechnol. May 1996;14(5):620-3.
Freeman et al., Four enzymes define the incorporation of coenzyme A in thienamycin biosynthesis. Proc Natl Acad Sci U S A. Aug. 12, 2008;105(32):11128-33. Epub Aug. 4, 2008.
Freeman et al., A comparison of methods for plasmid delivery into plant protoplasts. Plant Cell Physiol. 1984;25(8):1353-65.
Frenkel et al., 7,12-dimethylbenz[a]anthracene induces oxidative DNA modification in vivo. Free Radic Biol Med. Sep. 1995;19(3):373-80.
Friesen et al., Purification and Kinetic Characterization of CTP-:Phosphocholine Cytidylyltransferase from *Saccharomyces cerevisiae*. Protein Expression and Purification. Feb. 2001;21(1):141-8.
Fromm et al., Stable transformation of maize after gene transfer by electroporation. Nature. Feb. 27-Mar. 5, 1986;319(6056):791-3.
Fujio et al., Construction of a plasmid carrying both CTP synthetase and a fused gene formed from cholinephosphate cytidylyltransferase and choline kinase genes and its application to industrial CDP-choline production: enzymatic production of CDP-choline from orotic acid (Part II). Biosci Biotechnol Biochem. Jun. 1997;61(6):960-4.
Gaspar et al., High yields of 2,3-butanediol and mannitol in *Lactococcus lactis* through engineering of NAD$^+$ cofactor recycling. Appl Environ Microbiol. Oct. 2011;77(19):6826-35. Epub Aug. 12, 2011. Supplemental material included.
Ger et al., A single Ser-180 mutation desensitizes feedback inhibition of the phenylalanine-sensitive3-deoxy-D-arabino-heptulosonate 7-phosphate (DAHP) synthetase in *Escherichia coli*. J Biochem. Nov. 1994;116(5):986-90.
Gibellini et al., Biochemical characterization of the initial steps of the Kennedy pathway in *Trypanosoma brucei*: the ethanolamine and choline kinases. Biochem J. 2008;415:135-44. Supplemental data attached.
Goerke et al., Development of cell-free protein synthesis platforms for disulfide bonded proteins. Biotechnol Bioeng. Feb. 1, 2008;99(2):351-67. Epub Jul. 11, 2007.
Gordon-Kamm et al., Transformation of Maize Cells and Regeneration of Fertile Transgenic Plants. Plant Cell. Jul. 1990;2(7):603-618.
Gosset et al., A direct comparison of approaches for increasing carbon flow to aromatic biosynthesis in *Escherichia coli*. J Ind Microbiol. Jul. 1996;17(1):47-52.
Grabowski, Enantiopure drug synthesis: from methyldopa to imipenem to efavirenz. Chirality. 2005;17 Suppl:S249-59.
Grieco et al., .beta.-Lactam antibiotics: a formal stereocontrolled total synthesis of (.+-.)-thienamycin. J Am Chem Soc. 1984;106(21):6414-7.
Grunstein et al., Colony hybridization: a method for the isolation of cloned DNAs that contain a specific gene. Proc Natl Acad Sci U S A. Oct. 1975;72(10):3961-5.
Hamed et al., Carboxymethylproline synthase catalysed syntheses of functionalized N-heterocycles. Chem Commun (Camb). Mar. 7, 2010;46(9):1413-5. Epub Jan. 12, 2010.
Hamed et al., Evidence that thienamycin biosynthesis proceeds via C-5 epimerization: I catalyzes the formation of (2S,5S)-trans-carboxymethylproline. Chembiochem. Jan. 26, 2009;10(2):246-50.
Hawley et al., Compilation and analysis of *Escherichia coli* promoter DNA sequences. Nucleic Acids Res. Apr. 25, 1983;11(8):2237-55.
Herrmann, The shikimate pathway as an entry to aromatic secondary metabolism. Plant Physiol. Jan. 1995;107(1):7-12.

(56) References Cited

OTHER PUBLICATIONS

Hikita et al., Effects of total hydrophobicity and length of the hydrophobic domain of a signal peptide on in vitro translocation efficiency. J Biol Chem. 1992;267:4882-8.

Hikita et al., The requirement of a positive charge at the amino terminus can be compensated for by a longer central hydrophobic stretch in the functioning of signal peptides. J Biol Chem. 1992;267:12375-9.

Hodgson et al., π-Allyltricarbonyliron lactone complexes in synthesis: application to the synthesis of the β-lactam antibiotic (+)-thienamycin. J Chem Soc Chem Comm. 1984;8:494-6.

Inouye, The discovery of mRNA interferases: implication in bacterial physiology and application to biotechnology. J Cell Physiol. Dec. 2006;209(3):670-6.

Ishii et al., DBTBS: a database of *Bacillus subtilis* promoters and transcription factors. Nucleic Acids Res. Jan. 1, 2001;29(1):278-80.

Jacobi et al., Formal Total Syntheses of the β-Lactam Antibiotics Thienamycin and PS-5. J Org Chem. 1996;61(7):2413-27.

Jang et al., Sugar sensing in higher plants. Plant Cell. Nov. 1994;6(11):1665-79.

Jermutus et al., Recent advances in producing and selecting functional proteins by using cell-free translation. Curr Opin Biotechnol. Oct. 1998;9(5):534-48.

Jewett et al., An integrated cell-free metabolic platform for protein production and synthetic biology. Mol Syst Biol. 2008;4:220. Epub Oct. 14, 2008.

Jewett et al., Mimicking the *Escherichia coli* cytoplasmic environment activates long-lived and efficient cell-free protein synthesis. Biotechnol Bioeng. Apr. 5, 2004;86(1):19-26.

Kahan et al., Thienamycin, a new beta-lactam antibiotic. I. Discovery, taxonomy, isolation and physical properties. J Antibiot (Tokyo). Jan. 1979;32(1):1-12.

Kahan et al., Thienamycin: development of imipenen-cilastatin. J Antimicrob Chemother. Dec. 1983;12 Suppl D:1-35.

Kalderon et al., A short amino acid sequence able to specify nuclear location. Cell. Dec. 1984;39(3 Pt 2):499-509.

Icametani et al., Studies on the syntheses of heterocyclic compounds. 800. A formal total synthesis of (.+-.)-thienamycin and a (.+-.)-decysteaminylthienamycin derivative. J Am Chem Soc. 1980;102(6):2060-5.

Kapust et al., Tobacco etch virus protease: mechanism of autolysis and rational design of stable mutants with wild-type catalytic proficiency. Protein Eng. Dec. 2001;14(12):993-1000.

Kikuchi et al., Mutational analysis of the feedback sites of phenylalanine-sensitive 3-deoxy-D-arabino-heptulosonate-7-phosphate synthase of *Escherichia coli*. Appl Environ Microbiol. Feb. 1997;63(2):761-2.

Kim et al., Expression, purification, and characterization of choline kinase, product of the cki gene from *Saccharomyces cerevisiae*. J Bio Chem. 1998;273(12):6844-6852.

Kim et al., Prolonged cell-free protein synthesis using dual energy sources: Combined use of creatine phosphate and glucose for the efficient supply of ATP and retarded accumulation of phosphate. Biotechnol Bioeng. Aug. 15, 2007;97(6):1510-5.

Kimmel, Identification and characterization of specific clones: strategy for confirming the validity of presumptive clones. Methods Enzymol. 1987;152:507-11.

Kindle, High-frequency nuclear transformation of *Chlamydomonas reinhardtii*. Proc Natl Acad Sci U S A. Feb. 1990;87(3):1228-32.

Knapp et al., Cell-free production of active *E. coli* thioredoxin reductase and glutathione reductase. FEBS Lett. Feb. 13, 2004;559(1-3):66-70.

Knop et al., Hydroaromatic equilibration during biosynthesis of shikimic acid. J Am Chem Soc. Oct. 24, 2001;123(42):10173-82.

Ko et al., Targeting of proteins to the thylakoid lumen by the bipartite transit peptide of the 33 kd oxygen-evolving protein. EMBO J. Nov. 1989;8(11):3187-94.

Krämer et al., Metabolic engineering for microbial production of shikimic acid. Metab Eng. Oct. 2003;5(4):277-83.

Kumagai et al., Current status of oral carbapenem development. Curr Med Chem—Anti-Infective Agents. Jan. 2002;1(1):1-14.

Kunkel, Rapid and efficient site-specific mutagenesis without phenotypic selection. Proc Natl Acad Sci U S A. Jan. 1985;82(2):488-92.

Lee et al., Fermentative production of thymidine by a metabolically engineered *Escherichia coli* strain. Appl Environ Microbiol. Apr. 2009;75(8):2423-32. Epub Feb. 27, 2009.

Lee et al., Systems metabolic engineering of *Escherichia coli* for L-threonine production. Mol Syst Biol. 2007;3:149. Epub Dec. 4, 2007.

Lee, High cell-density culture of *Escherichia coli*. Trends Biotechnol. Mar. 1996;14(3):98-105.

Liu et al., Streamlining *Escherichia coli* S30 extract preparation for economical cell-free protein synthesis. Biotechnol Prog. Mar.-Apr. 2005;21(2):460-5.

Ludwig et al., Mutations affecting export and activity of cytolysin A from *Escherichia coli*. J Bacteriol. Aug. 2010;192(15):4001-11. Epub May 28, 2010.

Mackle et al., Role of signal peptides in targeting of proteins in cyanobacteria. J Bacteriol. Apr. 1994;176(7):1857-64.

Mandel et al., Modular synthesis of pantetheine and phosphopantetheine. Org Lett. Dec. 23, 2004;6(26):4801-3.

Martin et al., Engineering a mevalonate pathway in *Escherichia coli* for production of terpenoids. Nat Biotechnol. Jul. 2003;21(7):796-802. Epub Jun. 1, 2003.

Mergulhão et al., Analysis of factors affecting the periplasmic production of recombinant proteins in *Escherichia coli*. J Microbiol Biotechnol. Aug. 2007;17(8):1236-41.

Mergulhão et al., Recombinant protein secretion in *Escherichia coli*. Biotechnol Adv. May 2005;23(3):177-202. Epub Jan. 8, 2005.

Meyerhof, New investigations in the kinetics of cell free alcoholic fermentation. Antonie Van Leeuwenhoek. Jan.-Apr. 1947;12(1-4):140-4.

Michel-Reydellet et al., Amino acid stabilization for cell-free protein synthesis by modification of the *Escherichia coli* genome. Metab Eng. Jul. 2004;6(3):197-203.

Muchmore et al., Crystal structure of glutamine phosphoribosylpyrophosphate amidotransferase from *Escherichia coli*. Protein Sci. Jan. 1998;7(1):39-51.

Muktiono et al., Isolation and purification assay of ex vivo photosystem II D1 protein toward integrated biointeraction analysis. Anal Bioanal Chem. Feb. 2008;390(4):1195-202. Epub Jan. 3, 2008.

Murphy, Use of bacteriophage lambda recombination functions to promote gene replacement in *Escherichia coli*. J Bacteriol. Apr. 1998;180(8):2063-71.

Myers et al., Determination of imipenem and cilastatin in serum by high-pressure liquid chromatography. Antimicrob Agents Chemother. Jul. 1984;26(1):78-81.

Narang et al., Improved phosphotriester method for the synthesis of gene fragments. Methods Enzymol. 1979;68:90-8.

Neidhardt et al., Culture medium for enterobacteria. J Bacteriol. Sep. 1974;119(3):736-47.

Nunez et al., The Biosynthetic Gene Cluster for the β-Lactam Carbapenem Thienamycin in *Streptomyces cattleya*. Chem Biol. Apr. 2003;10(4):301-11.

Ono et al., Photosynthetic electron transport and phosphorylation reactions in thylakoid membranes from the blue-green alga Anacystis nidulans. Biochim Biophys Acta. Jun. 8, 1978;502(3):477-85.

Park et al., Metal-catalyzed oxidation of phenylalanine-sensitive 3-deoxy-D-arabino heptulosonate-7-phosphate synthase from *Escherichia coli*: inactivation and destabilization by oxidation of active-site cysteines. J Bacteriol. Mar. 1999;181(5):1636-42.

Patnaik et al., Engineering of *Escherichia coli* central metabolism for aromatic metabolite production with near theoretical yield. Appl Environ Microbiol. Nov. 1994;60(11):3903-8.

Pitera et al., Balancing a heterologous mevalonate pathway for improved isoprenoid production in *Escherichia coli*. Metab Eng. Mar. 2007;9(2):193-207. Epub Nov. 23, 2006.

Qi et al., A one-step PCR-based method for rapid and efficient site-directed fragment deletion, insertion, and substitution mutagenesis. J Virolog Meth. Apr. 2008;149(1):85-90.

(56) References Cited

OTHER PUBLICATIONS

Ray et al., Mutational analysis of the catalytic and feedback sites of the tryptophan-sensitive 3-deoxy-D-arabino-heptulosonate-7-phosphate synthase of *Escherichia coli*. J Bacteriol. Dec. 1988;170(12):5500-6.
Reider et al., Total synthesis of thienamycin: a new approach from aspartic acid. Tetra Lett. 1982;23(22):2293-6.
Reyes et al., Genomic library screens for genes involved in n-butanol tolerance in *Escherichia coli*. PloS One. Mar. 8, 2011;6(3):e17678.
Rodríguez et al., Identification of transcriptional activators for thienamycin and cephamycin C biosynthetic genes within the thienamycin gene cluster from *Streptomyces cattleya*. Mol Microbiol. Aug. 2008;69(3):633-45.
Rodríguez et al., Transcriptional organization of ThnI-regulated thienamycin biosynthetic genes in *Streptomyces cattleya*. J Antibiot (Tokyo). Mar. 2010;63(3):135-8. Epub Jan. 22, 2010.
Sagui et al., Enzymatic synthesis of ω-carboxy-β-hydroxy-(1)-α-amino acids. Tetrahedron. May 26, 2008;64(22):5079-84.
Salis et al., Automated design of synthetic ribosome binding sites to control protein expression. Nat Biotechnol. Oct. 2009;27(10):946-50. Epub Oct. 4, 2009.
Salzmann et al., A stereocontrolled synthesis of (+)-thienamycin. J Am Chem Soc. 1980;102(19);6161-3.
Salzmann et al., A stereocontrolled, enantiomerically specific total synthesis of thienamycin. Philos Trans R Soc Lond B Biol Sci. May 16, 1980;289(1036):191-5.
Sarath et al., Use of GFP as a reporter for the analysis of sequence-specific proteases. Curr Protoc Protein Sci. Feb. 2001;Chapter 21 Unit 9 Suppl. 26: 21.9.1-.10.
Sato et al., Poly[(R)-3-hydroxybutyrate] formation in *Escherichia coli* from glucose through an enoyl-CoA hydratase-mediated pathway. J Biosci Bioeng, Jan. 2007;103(1):38-44.
Schlehuber et al., Prediction and identification of a permissive epitope insertion site in the vesicular stomatitis virus glycoprotein. J Virol. May 2004;78(10):5079-87.
Schnell, Protein targeting to the thylakoid membrane. Annu Rev Plant Physiol Plant Mol Biol. Jun. 1998;49:97-126.
Scopes, Glycolysis in cell-free systems. New beer in an old bottle: Eduard Buchner and the growth of biochemical knowledge. Ed A. Cornish-Bowden. 1997;151-8.
Sheen, Metabolic repression of transcription in higher plants. Plant Cell. Oct. 1990;2(10):1027-38.
Shi et al., Molecular properties, functions, and potential applications of NAD kinases. Acta Biochim Biophys Sin (Shanghai). May 2009;41(5):352-61.
Shine et al., Determinant of cistron specificity in bacterial ribosomes. Nature. Mar. 6, 1975;254(5495):34-8.
Simmons et al., Translational level is a critical factor for the secretion of heterologous proteins in *Escherichia coli*. Nat Biotechnol. May 1996;14(5):629-34.
Sleeman et al., Carboxymethylproline synthase (CarB), an unusual carbon-carbon bond-forming enzyme of the crotonase superfamily involved in carbapenem biosynthesis. J Biol Chem. Feb. 20, 2004;279(8):6730-6. Epub Nov. 18, 2003.
Soares et al., Periplasmic expression of human growth hormone via plasmid vectors containing the lambdaPL promoter: use of HPLC for product quantification. Protein Eng. Dec. 2003;16(12):1131-8.
Sorci et al., Nicotinamide mononucleotide synthetase is the key enzyme for an alternative route of NAD biosynthesis in *Francisella tularensis*.Proc Natl Acad Sci U S A. Mar. 3, 2009;106(9):3083-8. Epub Feb. 9, 2009. Supporting information attached.
Stadtman et al., Metal-catalyzed oxidation of proteins. Physiological consequences. J Biol Chem. Feb. 5, 1991;266(4):2005-8.
Stapon et al., Synthesis of (3S,5R)-carbapenam-3-carboxylic acid and its role in carbapenem biosynthesis and the stereoinversion problem. J Am Chem Soc. Dec. 24, 2003;125(51):15746-7.
Stephanopoulos et al., Exploiting biological complexity for strain improvement through systems biology. Nat Biotechnol. Oct. 2004;22(10):1261-7.

Suzuki et al., Single protein production (SPP) system in *Escherichia coli*. Nat Protoc. 2007;2(7):1802-10.
Suzuki et al., Single protein production in living cells facilitated by an mRNA interferase. Mol Cell. Apr. 15, 2005;18(2):253-61.
Swartz et al., Advances in *Escherichia coli* production of therapeutic proteins. Curr Opin Biotechnol. Apr. 2001;12(2):195-201.
Swartz, Developing cell-free biology for industrial applications. J Ind Microbiol Biotechnol. Jul. 2006;33(7):476-85. Epub May 9, 2006. Review.
Sybesma et al., Increased production of folate by metabolic engineering of *Lactococcus lactis*. Appl Environ Microbiol. Jun. 2003;69(6):3069-76.
Tjalsma et al., Proteomics of protein secretion by *Bacillus subtilis*: separating the "secrets" of the secretome. Microbiol Mol Biol Rev. Jun. 2004;68(2):207-33.
Tracewell et al., Directed enzyme evolution: climbing fitness peaks one amino acid at a time. Curr Opin Chem Biol. Feb. 2009;13(1):3-9. Epub Feb. 25, 2009.
Tyo et al., Analysis of polyhydroxybutyrate flux limitations by systematic genetic and metabolic perturbations. Metab Eng. May 2010;12(3):187-95. Epub Oct. 30, 2009.
Van Bloois et al., Export of functional *Streptomyces coelicolor* alditol oxidase to the periplasm or cell surface of *Escherichia coli* and its application in whole-cell biocatalysis. Appl Microbiol Biotechnol. Jun. 2009;83(4):679-87. Epub Feb. 18, 2009.
Van Hees et al., Determination of low molecular weight organic acids in soil solution by HPLC. Talanta. Jan. 5, 1999;48(1):173-9.
Voloshin et al., Efficient and scalable method for scaling up cell free protein synthesis in batch mode. Biotechnol Bioeng. Aug. 20, 2005;91(4):516-21.
Wahl et al., Molecular hybridization of immobilized nucleic acids: theoretical concepts and practical considerations. Methods Enzymol. 1987;152:399-407.
Weaver et al., Cloning of an aroF allele encoding a tyrosine-insensitive 3-deoxy-D-arabino-heptulosonate 7-phosphate synthase. J Bacteriol. Nov. 1990;172(11):6581-4.
Welch et al., Studies on cell-free metabolism: Ethanol production by a yeast glycolytic system reconstituted from purified enzymes. J Biotechnol. 1985;2:257-73.
Wiechert et al., A universal framework for 13C metabolic flux analysis. Metab Eng. Jul. 2001;3(3):265-83.
Wiechert, 13C metabolic flux analysis. Metab Eng. Jul. 2001;3(3):195-206.
Wilen et al., Tetrahedron report No. 38: Strategies in optical resolutions. Tetrahedron. 1977;33:2725-2736.
Williamson et al., Biosynthesis of the beta-lactam antibiotic, thienamycin, by *Streptomyces cattleya*. J Biol Chem. Apr. 25, 1985;260(8):4637-47.
Wilson et al., The shikimic acid pathway and polyketide biosynthesis. J Indust Microbiol Biotechnol. 1998;20:299-303.
Withers et al., Identification of isopentenol biosynthetic genes from *Bacillus subtilis* by a screening method based on isoprenoid precursor toxicity. Appl Environ Microbiol. Oct. 2007;73(19):6277-83. Epub Aug. 10, 2007.
Woodrow et al., A sequential expression system for high-throughput functional genomic analysis. Proteomics. Nov. 2007;7(21):3870-9.
Woodrow et al., Rapid expression of functional genomic libraries. J Proteome Res. Dec. 2006;5(12):3288-300.
Wylie et al., A single point mutation in ctp synthetase of chlamydia trachomatis confers resistance to cyclopentenyl cytosine. J Biol Chem. 1996;271:15393-400.
Yamaguchi et al., MqsR, a crucial regulator for quorum sensing and biofilm formation, is a GCU-specific mRNA interferase in *Escherichia coli*. J Biol Chem. Oct. 16, 2009;284(42):28746-53. Epub Aug. 18, 2009.
Yamaguchi et al., mRNA interferases, sequence-specific endoribonucleases from the toxin-antitoxin systems. Prog Mol Biol Transl Sci. 2009;85:467-500.
Yang et al., Export of methyl parathion hydrolase to the periplasm by the twin-arginine translocation pathway in *Escherichia coli*. J Agric Food Chem. Oct. 14, 2009;57(19):8901-5.

(56) References Cited

OTHER PUBLICATIONS

Yang et al., Rapid expression of vaccine proteins for B-cell lymphoma in a cell-free system. Biotechnol Bioeng. Mar. 5, 2005;89(5):503-11.
Yeo et al., Plasmodium falciparum CTP:phosphocholine cytidylyltransferase expressed in *Escherichia coli*: purification, characterization and lipid regulation. Biochem J. 1997;324:903-10.
Zamboni et al., (13)C-based metabolic flux analysis. Nat Protoc. 2009;4(6):878-92. Epub May 21, 2009.
Zawada et al., Effects of growth rate on cell extract performance in cell-free protein synthesis. Biotechnol Bioeng. Jul. 5, 2006;94(4):618-24.
Zawada et al., Maintaining rapid growth in moderate-density *Escherichia coli* fermentations. Biotechnol Bioeng. Feb. 20, 2005;89(4):407-15.
Zhang et al., Characterization of ChpBK, an mRNA interferase from *Escherichia coli*. J Biol Chem. Jul. 15, 2005;280(28):26080-8. Epub May 18, 2005.
Zhang et al., Characterization of YafO, an *Escherichia coli* toxin. J Biol Chem. Sep. 18, 2009;284(38):25522-31. Epub Jul. 17, 2009.
Zhang et al., Efficient regeneration of transgenic plants from rice protoplasts and correctly regulated expression of the foreign gene in the plants. Theor Appl Genet. 1988;76(6):835-40.
Zhang et al., Insights into the mRNA cleavage mechanism by MazF, an mRNA interferase. J Biol Chem. Feb. 4, 2005;280(5):3143-50. Epub Nov. 10, 2004.
Ward et al., Genomic insights into methanotrophy: the complete genome sequence of *Methylococcus capsulatus* (Bath). PLOS Biology. 2004;2(10):1616-28.
Invitation to Pay Additional Fees for PCT/US2012/054195, mailed Jan. 30, 2013.
International Search Report and Written Opinion for PCT/US2012/054195, mailed Apr. 12, 2013.
International Preliminary Report on Patentability for PCT/US2011/035639, mailed Nov. 22, 2012.
International Search Report and Written Opinion for PCT/US2011/049997, mailed Dec. 13, 2011.
International Preliminary Report on Patentability for PCT/US2011/049997, mailed Mar. 14, 2013.
Extended European Search Report for EP 09836804.6, mailed Jun. 4, 2012.
Office Action, mailed Jul. 2, 2012 for U.S. Appl. No. 12/644,998.
Office Action, mailed Dec. 4, 2012 for U.S. Appl. No. 12/644,998.
GENBANK Submission; NIH/NCBI, Accession No. AAB59985; Ling et al.; Nov. 24, 1994.
GENBANK Submission; NIH/NCBI, Accession No. AAC73225; Blattner et al.; Sep. 1, 2011.
GENBANK Submission; NIH/NCBI, Accession No. AAC73226; Blattner et al.; Sep. 1, 2011.
GENBANK Submission; NIH/NCBI, Accession No. AAC73296; Blattner et al.; Sep. 1, 2011.
GENBANK Submission; NIH/NCBI, Accession No. AAC73346; Blattner et al.; Sep. 1, 2011.
GENBANK Submission; NIH/NCBI, Accession No. AAC73347; Blattner et al.; Sep. 1, 2011.
GENBANK Submission; NIH/NCBI, Accession No. AAC73842; Blattner et al.; Sep. 1, 2011.
GENBANK Submission; NIH/NCBI, Accession No. AAC73957; Blattner et al.; Sep. 1, 2011.
GENBANK Submission; NIH/NCBI, Accession No. AAC74746; Blattner et al.; Sep. 1, 2011.
GENBANK Submission; NIH/NCBI, Accession No. AAC74849; Blattner et al.; Sep. 1, 2011.
GENBANK Submission; NIH/NCBI, Accession No. AAC74924; Blattner et al.; Sep. 1, 2011.
GENBANK Submission; NIH/NCBI, Accession No. AAC75447; Blattner et al.; Sep. 1, 2011.
GENBANK Submission; NIH/NCBI, Accession No. AAC75821; Blattner et al.; Sep. 1, 2011.
GENBANK Submission; NIH/NCBI, Accession No. AAC75962; Blattner et al.; Sep. 1, 2011.
GENBANK Submission; NIH/NCBI, Accession No. AAC75963; Blattner et al.; Sep. 1, 2011.
GENBANK Submission; NIH/NCBI, Accession No. AAC76849; Blattner et al.; Sep. 1, 2011.
GENBANK Submission; NIH/NCBI, Accession No. AAC76898; Blattner et al.; Sep. 1, 2011.
GENBANK Submission; NIH/NCBI, Accession No. AAC76901; Blattner et al.; Sep. 1, 2011.
GENBANK Submission; NIH/NCBI, Accession No. AAC76995; Blattner et al.; Sep. 1, 2011.
GENBANK Submission; NIH/NCBI, Accession No. AAD38229; McGowan et al.; Jul. 14, 1999.
GENBANK Submission; NIH/NCBI, Accession No. AAD38230; McGowan et al.; Jul. 14, 1999.
GENBANK Submission; NIH/NCBI, Accession No. AAD38231; McGowan et al.; Jul. 14, 1999.
GENBANK Submission; NIH/NCBI, Accession No. ABA79923; Copeland et al.; Nov. 21, 2011.
GENBANK Submission; NIH/NCBI, Accession No. ACJ71669; Erb et al.; Dec. 10, 2008.
GENBANK Submission; NIH/NCBI, Accession No. AEW99093; Ou et al.; Dec. 29, 2011.
GENBANK Submission; NIH/NCBI, Accession No. AEW99097; Ou et al.; Dec. 29, 2011.
GENBANK Submission; NIH/NCBI, Accession No. AEW99098; Ou et al.; Dec. 29, 2011.
GENBANK Submission; NIH/NCBI, Accession No. BAA22406; Mori et al.; Sep. 20, 1997.
GENBANK Submission; NIH/NCBI, Accession No. BAB67276; Kawarabayasi et al.; Aug. 17, 2011.
GENBANK Submission; NIH/NCBI, Accession No. CAD18973; Nunez et al.; Apr. 15, 2005.
GENBANK Submission; NIH/NCBI, Accession No. CAD18975; Nunez et al.; Apr. 15, 2005.
GENBANK Submission; NIH/NCBI, Accession No. CAD18981; Nunez et al.; Apr. 15, 2005.
GENBANK Submission; NIH/NCBI, Accession No. CAD18985; Nunez et al.; Apr. 15, 2005.
GENBANK Submission; NIH/NCBI, Accession No. CAD18990; Nunez et al.; Apr. 15, 2005.
UniProtKB/Swiss-Prot; Accession No. P28269; Yonaha et al.; Jul. 11, 2012.
Baba et al., Construction of *Escherichia coli* K-12 in-frame, single-gene knockout mutants: the Keio collection. Mol Syst Biol. 2006;2:2006.0008. Epub Feb. 21, 2006.
Bodner et al., Definition of the common and divergent steps in carbapenem β-lactam antibiotic biosynthesis. Chembiochem. Sep. 19, 2011;12(14):2159-65. doi: 10.1002/cbic.201100366. Epub Aug. 24, 2011.
Bujara et al., Optimization of a blueprint for in vitro glycolysis by metabolic real-time analysis. Nat Chem Biol. May 2011;7(5):271-7. doi: 10.1038/nchembio.541. Epub Mar. 20, 2011.
Flores et al., Analysis of carbon metabolism in *Escherichia coli* strains with an inactive phosphotransferase system by (13)C labeling and NMR spectroscopy. Metab Eng. Apr. 2002;4(2):124-37.
Flores et al., Growth-rate recovery of *Escherichia coli* cultures carrying a multicopy plasmid, by engineering of the pentose-phosphate pathway. Biotechnol Bioeng. Aug. 20, 2004;87(4):485-94.
Fox et al., Methane monooxygenase from Methylosinus trichosporium OB3b. Purification and properties of a three-component system with high specific activity from a type II methanotroph. J Biol Chem. Jun. 15, 1989;264(17):10023-33.
Fradejas et al., The control of shikimic acid synthesis by tyrosine and phenylalamine. Biochem Biophys Res Commun. Jul. 26, 1961;5:320-3.
Hamed et al., Crotonase catalysis enables flexible production of functionalized prolines and carbapenams. J Am Chem Soc. Jan. 11, 2012;134(1):471-9. doi: 10.1021/ja208318d. Epub Dec. 14, 2011.
Hamed et al., The enzymes of β-lactam biosynthesis. Nat Prod Rep. Jan. 2013;30(1):21-107. doi: 10.1039/c2np20065a.

(56) References Cited

OTHER PUBLICATIONS

Kern et al., Engineering primary metabolic pathways of industrial micro-organisms. J Biotechnol. Mar. 30, 2007;129(1):6-29. Epub Dec. 2, 2006.

Luli et al., Comparison of growth, acetate production, and acetate inhibition of *Escherichia coli* strains in batch and fed-batch fermentations. Appl Environ Microbiol. Apr. 1990;56(4):1004-11.

Meynial-Salles et al., New tool for metabolic pathway engineering in *Escherichia coli*: one-step method to modulate expression of chromosomal genes. Appl Environ Microbiol. Apr. 2005;71(4):2140-4.

Niu et al., Benzene-free synthesis of adipic acid. Biotechnol Prog. Mar.-Apr. 2002;18(2):201-11.

Sauer et al., The soluble and membrane-bound transhydrogenases UdhA and PntAB have divergent functions in NADPH metabolism of *Escherichia coli*. J Biol Chem. Feb. 20, 2004;279(8):6613-9. Epub Dec. 3, 2003.

Swartz, Transforming biochemical engineering with cell-free biology. AIChE J. 2012;58(1):5-13.

Wang et al., Programming cells by multiplex genome engineering and accelerated evolution. Nature. Aug. 13, 2009;460(7257):894-8. Epub Jul. 26, 2009.

Yu et al., Production of high-quality particulate methane monooxygenase in high yields from *Methylococcus capsulatus* (bath) with a hollow-fiber membrane bioreactor. J Bacteriol. Oct. 2003;185(20):5915-24.

US 8,916,358 B2

METHODS FOR CONTROL OF FLUX IN METABOLIC PATHWAYS THROUGH PROTEASE MANIPULATION

RELATED APPLICATIONS

This application claims priority under 35 U.S.C. §119(e) to U.S. provisional application, U.S. Ser. No. 61/378,828, filed Aug. 31, 2010, which is incorporated herein by reference.

BACKGROUND OF THE INVENTION

Production of chemicals via synthetic enzymatic pathways in microbial hosts has proven useful for many important classes of molecules, including isoprenoids, polyketides, nonribosomal peptides, bioplastics, and chemical building blocks. Due to the inherent modularity of biological information, synthetic biology holds great potential for expanding this list of microbially produced compounds even further. Yet embedding a novel biochemical pathway in the metabolic network of a host cell can disrupt the subtle regulatory mechanisms that the cell has evolved over the millennia. Indeed, the final yield of a compound is often limited by deleterious effects on the engineered cell's metabolism that are difficult to predict due to the limited understanding of the complex interactions that occur within the cell. The unregulated consumption of cellular resources, metabolic burden of heterologous protein production, and accumulation of pathway intermediates/products that are inhibitory or toxic to the host are all significant issues that may limit overall yield.

The concept of metabolic engineering has emerged to fulfill this purpose, which can be defined as purposeful modification of metabolic and cellular networks by employing various experimental techniques to achieve desired goals. What distinguishes metabolic engineering from genetic engineering and strain improvement is that it considers metabolic and other cellular network as a whole to identify targets to be engineered. In this sense, metabolic flux is an essential concept in the practice of metabolic engineering. Although gene expression levels and the concentrations of proteins and metabolites in the cell can provide clues to the status of the metabolic network, they have inherent limitations in fully describing the cellular phenotype due to the lack of information on the correlations among these cellular components. Metabolic fluxes represent the reaction rates in metabolic pathways, and serve to integrate these factors through a mathematical framework. Thus, metabolic fluxes can be considered as one way of representing the phenotype of the cell as a result of interplays among various cell components; the observed metabolic flux profiles reflect the consequences of interconnected transcription, translation, and enzyme reactions incorporating complex regulations.

Cell-free synthesis offers advantages over in vivo production methods. Importantly, the lack of a cell wall in vitro allows for direct control of the synthesis environment. The redox potential, pH, or ionic strength can be altered directly, and over more broad, non-physiological ranges, due to lack of cell growth or need for cell viability. Furthermore, direct recovery of products can more easily be achieved. Cell-free systems can direct most, if not all, of the metabolic resources of the cell towards the exclusive production from one pathway. The present compositions and methods address these issues.

SUMMARY OF THE INVENTION

Systems, compositions, and methods are provided for controlling metabolic pathway flux through modification of targeted enzymes that compete with enzymes involved in a pathway of interest, including modification to maintain or alter cellular concentrations of the targeted enzymes during a cell growth phase, followed by manipulation to decrease concentrations of the targeted enzymes during a production phase, when the product of the pathway of interest is produced. The cell growth phase necessarily involves intact cells, while the production phase may be performed with lysates of such cells.

In the systems, compositions, and methods provided herein, target enzymes (e.g., enzymes that compete for substrates of enzymes in the pathway of interest) are targeted for cleavage by a site-specific protease. Such targeted enzymes are undesirable during production phase of the metabolic pathway. The targeted enzyme(s) may be genetically modified to comprise at least one cleavage site (also referred to herein as a site-specific protease recognition site) for a site-specific protease or may have a naturally-occurring cleavage site. The cleavage site is typically located such that native enzyme activity is minimally affected and that when the targeted enzyme is cleaved, it is inactivated.

The corresponding site-specific protease, i.e., the protease that recognizes the cleavage site on the targeted enzyme, is genetically modified to incorporate a peptide sequence that provides for relocation of the site-specific protease to a cellular or extra-cellular compartment other than the naturally-occurring compartment. When the site-specific protease is relocated during the cell growth phase of the cell cycle, it is not in contact with, and thus is not able to cleave, the targeted enzyme. When the cell is lysed prior to the metabolite production phase, the site-specific protease is brought into contact with and cleaves the targeted enzyme, thereby inactivating the targeted enzyme.

In some embodiments, the site-specific protease is sequestered in the periplasm. In other embodiments, the site-specific protease is secreted into the growth medium.

The site-specific protease may be endogenous to the cell, or the coding sequence of the site-specific protease may be introduced into the cell for expression.

In one aspect, provided here are cells genetically modified to comprise (i) a site-specific protease coding sequence comprising a relocation sequence; and (ii) a coding sequence for at least one targeted enzyme, which competes with an enzyme involved in a pathway of interest, wherein the targeted enzyme coding sequence comprises a site-specific protease recognition site. In some embodiments, the site-specific protease coding sequence is operably linked to an inducible promoter.

In some embodiments, the relocation sequence is a periplasmic targeting sequence. In some embodiments, the periplasmic targeting sequence is selected from the group consisting of:

| | |
|---|---|
| MKIKTGARILALSALTTMMFSASALA, | (SEQ ID NO: 1) |
| MKKTAIAIAVALAGFATVAQA, | (SEQ ID NO: 2) |
| MKQSTIALALLPLLFTPVTKA, | (SEQ ID NO: 3) |
| MMITLRKLPLAVAVAAGVMSAQAMA, | (SEQ ID NO: 4) |
| MNKKVLTLSAVMASMLFGAAAHA, | (SEQ ID NO: 5) |
| MKYLLPTAAAGLLLLAAQPAMA, | (SEQ ID NO: 6) |
| MKKNIAFLLASMFVFSIATNAYA | (SEQ ID NO: 7) |
| MKKIWLALAGLVLAFSASA, | (SEQ ID NO: 8) |

-continued

MMTKIKLLMLIIFYLIISASAHA,        (SEQ ID NO: 9)

MKQALRVAFGFLILWASVLHA,          (SEQ ID NO: 10)
and

MRVLLFLLLSLFMLPAFS.             (SEQ ID NO: 11)

In some embodiments, the site-specific protease coding sequence encodes a site-specific protease selected from the group consisting of TEV NIa, HRV 3C, Enterokinase, Factor Xa, and Thrombin.

In certain embodiments, the targeted enzyme coding sequence is genetically modified to comprise the site-specific protease recognition site.

In some embodiments, the targeted enzyme competes with an enzyme that increases the rate of precursor supplied to the pathway of interest. In some embodiments, the targeted enzyme competes with a key pathway entry enzyme.

In certain embodiments, the gene encoding the native counterpart enzyme is replaced with the DNA sequence coding for the targeted enzyme. In certain embodiments, the gene encoding the native counterpart enzyme is knocked out (e.g., inactivated or replaced by an inactive DNA molecule). In some embodiments, the targeted enzyme is over-expressed in the cell.

In particular embodiments, the site-specific protease or the targeted enzyme is present on either an episomal vector or a chromosome.

In certain embodiments, the pathway of interest is the synthesis of: a) an antibiotic; b) a biosurfactant; c) an amino acid; d) an organic acid; e) a fatty acid; f) an alcohol or polyol; g) a flavor or fragrance; h) a nucleotide; i) a vitamin; j) a pigment; k) a sugar or polysaccharide; l) a biopolymer or plastic; m) an *E. coli* metabolite; n) shikimic acid and/or shikimate; o) an isoprenoid or terpene; p) poly-3-hydroxybutyrate; or q) isobutanol and/or 1-butanol.

In some embodiments, the pathway of interest is the synthesis of shikimic acid and/or shikimate, an isoprenoid or terpene, poly-3-hydroxybutyrate, isobutanol, and/or 1-butanol.

In some embodiments, the cell growth medium has been modified by the addition or enhancement of a factor that increases or preserves the activity of the targeted enzyme.

In one aspect, provided herein are cell lysates of any of the cells described herein.

In another aspect, provided herein are systems for producing a product of a pathway of interest, the systems comprising one or more lysates of any of the cells described herein, and optionally one or more substrates, enzymes, nutrients, cofactors, buffers, reducing agents, and ATP generating systems.

In yet another aspect, provided herein are methods of producing a product of a pathway of interest, the method comprising growing any one of the cells described herein to a desired cell density, lysing at least a portion of the cells, and optionally combining the lysate with one or more substrates, enzymes, nutrients, co-factors, buffers, reducing agents, and/or ATP generating systems, wherein the enzymes in the pathway of interest catalyze production of the product and the site-specific protease cleaves the targeted enzyme. In some embodiments, the method further comprises combining the lysate with one or more additional cell lysates.

In still another aspect, provided herein are vectors that comprise a site-specific protease coding sequence comprising a relocation sequence, wherein, optionally, the coding sequence is operably linked to an inducible promoter.

DETAILED DESCRIPTION OF THE EMBODIMENTS

Figure 1:
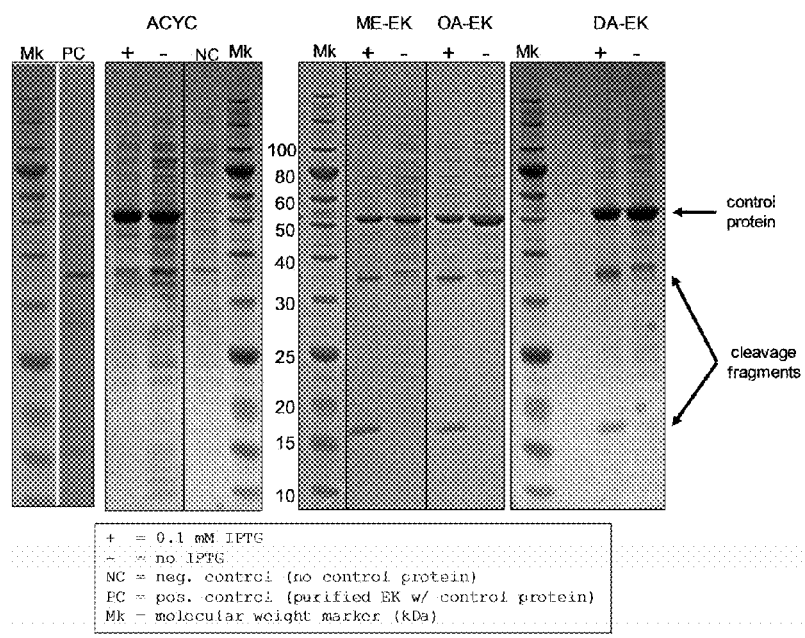
FIG. 1 depicts images of Coomassie stained poly-acrylamide gel electrophoresis (PAGE) gels of samples taken after cleavage incubations using cell extracts obtained from control cultures and from site-specific protease expression cultures with and without induction of site-specific protease expression. Abbreviations: pACYC-Duet vector control (ACYC); MalE-enterokinase, SEQ ID NO:19 (ME-EK); OmpA-enterokinase, SEQ ID NO:18 (OA-EK); DsbA-enterokinsae, SEQ ID NO:17 (DE-EK); and isopropyl β-D-1-thiogalactopyranoside (IPTG).

The systems, compositions, and methods described herein are based on the idea that genetically modified cells can be engineered for controlling metabolic pathway flux through genetic modification of targeted enzymes that compete with enzymes involved in a pathway of interest, including genetic modification to maintain or alter cellular concentrations of the targeted enzymes during a cell growth phase, followed by manipulation to decrease concentrations of the active targeted enzymes during the production phase, when the product of the pathway of interest is produced. During the production phase, targeted enzyme inactivation results from cleavage of the enzyme by a site-specific protease. The site-specific protease may be an endogenous or exogenous protease. In certain embodiments, the targeted enzyme is genetically modified to comprise a motif (e.g., a site-specific protease recognition site) that is cleaved by a site-specific protease.

In some embodiments, expression of the site-specific protease is inducible. In certain embodiments, the site-specific protease is genetically modified to be relocated to a cellular or extra-cellular compartment (e.g., a cellular or extra-cellular compartment) where the site-specific protease does not naturally occur, such that the site-specific protease does not inactivate the targeted enzyme when thus relocated. In certain embodiments, the site-specific protease is genetically modified to include a peptide sequence that provides for periplasmic targeting of the protease, that is where the protease is sequestered in the periplasm of the cell.

In certain embodiments, the targeted enzyme is one that competes with an enzyme involved in a pathway of interest. In some embodiments, the targeted enzyme competes with a pathway entry enzyme. In certain embodiments, the targeted enzyme competes with is a rate-limiting enzyme. In certain embodiments, the targeted enzyme competes with an enzyme that increases the rate of precursor supplied to the pathway of interest or that supplies another required substrate or cofactor.

In some embodiments, the gene encoding the native counterpart enzyme is replaced with the DNA sequence coding for the targeted enzyme. In certain embodiments, the gene encoding the native counterpart enzyme is knocked out (e.g., inactivated or replaced by artificial DNA). In certain embodiments, the targeted enzyme is over-expressed (e.g., enzyme expression is increased above physiologically-normal enzyme expression levels) in the cell.

In certain embodiments, the targeted enzyme and/or the site-specific protease is present on either an episomal vector or a chromosome.

In certain embodiments, the cell growth medium has been modified by the addition or enhancement of a factor (e.g., a nutrient, co-factor, reducing agent) that increases or preserves the activity of the targeted enzyme.

In one aspect, provided is a genetically modified cell, which comprises a site-specific protease modified to comprise a relocation sequence, e.g., a periplasmic targeting sequence. The cell may further comprise a targeted enzyme that has been genetically modified to introduce a recognition sequence for the site-specific protease, which inactivates the targeted enzyme upon cleavage.

In another aspect, lysates of such a genetically modified cell are provided. The lysate may be combined with one or more of substrate, nutrients, cofactors, buffers, reducing agents, ATP generating systems, and/or other agents to generate a cell-free system for producing a product of interest.

In another aspect, provided are methods for producing a product of interest, the method comprising growing cells that express a site-specific protease genetically modified to incorporate a peptide sequence that provides for its relocation, wherein a targeted enzyme comprising a recognition sequence for the site-specific protease is expressed in the cytoplasm of the cell, lysing the cells to bring the site-specific protease into contact with the targeted enzyme, and producing the product of the pathway in a cell-free system comprising the lysate. Additional substrate, nutrients, cofactors, buffers, reducing agents, ATP generating systems, and/or other agents, may be added to the cell-free system. In one embodiment the product of interest is produced at a high flux rate.

In yet another aspect, provided are methods for producing a product of interest, the method comprising growing cells that are genetically modified to over-express at least one periplasmic targeted site-specific protease, lysing the cells, and producing the product of the pathway of interest in a cell-free system comprising the lysate. Additional substrate, nutrients, cofactors, buffers, reducing agents, ATP generating systems, and/or other agents may be added to the cell-free system.

Production Methods

High yield production of a product of interest is accomplished by providing a cell in which cytoplasmic enzymes comprising a pathway of interest are expressed, e.g., at physiologically normal levels, or at greater than physiologically normal levels; and where at least one targeted enzyme involved in the pathway is (a) expressed at normal levels and (b) comprises an inactivating recognition for a site-specific protease. In some embodiments, the site-specific protease is expressed in the cell but relocated to a site where it does not contact the target enzyme.

During cell culture it may be desirable to control the components of the growth medium of the cells in order to avoid exposure of the periplasmic sequestered protease to conditions that affect activity, e.g., exposure to metals and the like. For example, it has been found that DAHP synthase in the shikimic acid pathway can be inactivated through copper-catalyzed oxidation, and thus it is desirable to modify the culture conditions by increasing the concentration of co-factors, such as manganese and magnesium metals, in the growth medium to outcompete available copper (see, e.g., Bauerle et al., *J. Bacteriol.* (1999) 181:1636-1642; and Stadtman et al., *J. Biol. Chem.* (1991) 266:2005-2008, each incorporated herein by reference). Thus, in certain embodiments, cofactor(s) are provided or concentrations of co-factor(s) are altered in the growth medium to enhance enzyme activation in the periplasm or other relocated enzyme site.

For production purposes, a lysate of the cell is utilized, wherein the periplasmically sequestered site-specific protease is brought into operable contact with the enzymes of the pathway of interest expressed in the cytoplasm. Cells are lysed by any convenient method that substantially maintains enzyme activity, e.g., sonication, French press, and the like, as known in the art. The lysate may be fractionated, particulate matter spun out, or may be used in the absence of additional processing steps. The cell lysate may be further combined with one or more substrates, enzymes, nutrients, co-factors, buffers, reducing agents, and/or ATP generating systems, as required for enzyme activity. Such a system, in certain embodiments, may be referred to herein as a "cell-free system," e.g., an isolated system containing a cell lysate or extract expressly engineered to synthesize an enzyme or cascade of enzymes that, when acting in a given sequence (e.g., in an enzymatic pathway) and proportion over a determined substrate, results in the preferential generation of a product, the compound of interest. A compound of interest may be a chemical entity (e.g., a small organic molecule), which can be used as an active pharmaceutical ingredient (API), chemical precursor, or intermediate.

As used herein, a "substrate" is a compound or mixture of compounds capable of providing the required elements needed to synthesize a compound of interest.

As used herein, a "small organic molecule" or "small molecule" refers to an organic molecule with a molecular weight of less than 800 g/mol (e.g., less than 700 g/mol, less than 600 g/mol, less than 500 g/mol, less than 400 g/mol, less than 300 g/mol, less than 200 g/mol, less than 100 g/mol, between 50 to 800 g/mol, inclusive, between 100 to 800 g/mol, inclusive, or between 100 to 500 g/mol, inclusive). In certain embodiments, the small organic molecule is a therapeutically active agent such as a drug (e.g., a small organic molecule approved by the U.S. Food and Drug Administration as provided in the Code of Federal Regulations (CFR)). The small organic molecule may also comprise a metal. In this instance, the small organic molecule is also referred to as an "small organometallic molecule."

As used herein, a "reducing equivalent" or "reducing agent" is a chemical species which transfers the equivalent of one electron in a redox reaction. Examples of reducing equivalents are a lone electron (for example in reactions involving metal ions), a hydrogen atom (consisting of a proton and an electron), and a hydride ion (:H—) which carries two electrons (for example in reactions involving nicotinamide adenine dinucleotide ($NAD^+$)). A "reducing equivalent acceptor" is a chemical species that accepts the equivalent of one electron in a redox reaction.

As used herein, an "adenosine triphosphate regeneration system" or "ATP regeneration system" is a chemical or biochemical system that converts adenosine, AMP, and ADP into ATP. Examples of ATP regeneration systems include those involving glucose metabolism, glutamate metabolism, and photosynthesis.

Lysates of cells of different genetic backgrounds (e.g. previously altered or genetically engineered) or species, or that are prepared by different strategies can be mixed and simultaneously or sequentially used in a process with the cell lysate. The lysate can be free or immobilized, and can be reused or disposed of at each stage of the process. For example, in certain embodiments, the cell lysate is a lysate of an *E. coli* organism engineered to overexpress one or more enzymes in the pathway of interest. In certain embodiments, the cell lysate is a combination of different cell lysates, e.g., a combination of two, three, four, five, six, seven, eight, nine, or ten different cell lysates, obtained from two, three, four, five, six, seven, eight, nine, or ten different *E. coli* organisms each engineered to overexpress one or more enzymes in the pathway of interest.

The methods described herein provide for high yields of the desired product, which yield is greater than the yield that can be achieved with a native microbial host. Productivity (i.e., rate of production per unit of volume or biomass) may also be increased. In one embodiment, the yield of product is at least about 2-fold above the basal rate, at least about 5-fold above the basal rate, at least about 10-fold above the basal rate, at least about 25-fold above the basal rate, at least about 50-fold above the basal rate, or more, e.g., between about 2-fold to about 100-fold above the basal rate. In certain embodiments, the rate of yield of the product using the inventive methods is between about 0.1 to 20 grams of product/L/h.

Different inocula can be adapted to different conditions (e.g., two batches grown on two different carbon sources) or can have different genotypes and then mixed to carry out the process (e.g., to get simultaneous consumption of a mix of carbon sources or sequential processing of a metabolite through a pathway divided into two separate batches of cells). A process can also take place sequentially by allowing one set of reactions to proceed in one vessel and then transferring the supernatant to a second vessel.

The reactions may utilize a large scale reactor, small scale, or may be multiplexed to perform a plurality of simultaneous syntheses. Continuous reactions will use a feed mechanism to introduce a flow of reagents, and may isolate the end-product as part of the process. Batch systems are also of interest, where additional reagents may be introduced over time to prolong the period of time for active synthesis. A reactor may be run in any mode such as batch, extended batch, semi-batch, semi-continuous, fed-batch, and continuous, and which will be selected in accordance with the application purpose.

The reactions may be of any volume, either in a small scale (e.g., usually at least about 1 ml and not more than about 15 ml) or in a scaled up reaction (e.g., where the reaction volume is at least about 15 ml, usually at least about 50 ml, more usually at least about 100 ml, and may be 500 ml, 1000 ml, or greater up to many thousands of liters of volume). Reactions may be conducted at any scale.

Various salts and buffers may be included, where ionic species may be optimized with regard to product production. When changing the concentration of a particular component of the reaction medium another component may be changed accordingly. Also, the concentration levels of components in the reactor may be varied over time. The adjuster of the thiol/disulfide oxidation/reduction potential may be dithiothreitol, ascorbic acid, glutathione, and/or their oxidized forms. Other adjusters of the general redox potential may also be used.

In a semi-continuous operation mode, the reactor may be operated in dialysis, diafiltration batch or fed-batch mode. A feed solution may be supplied to the reactor through the same membrane or a separate injection unit. Synthesized product is accumulated in the reactor, and then is isolated and purified according to the usual method for purification after completion of the system operation. Alternatively, product can be removed during the process either in a continuous or discontinuous mode with the option of returning part or all of the remaining compounds to the reactor.

Where there is a flow of reagents, the direction of liquid flow can be perpendicular and/or tangential to a membrane. Tangential flow is effective for recycling ATP and for preventing membrane plugging and may be superimposed on perpendicular flow. Flow perpendicular to the membrane may be caused or effected by a positive pressure pump or a vacuum suction pump or by applying trans-membrane pressure using other methods known in the art. The solution in contact with the outside surface of the membrane may be cyclically changed, and may be in a steady tangential flow with respect to the membrane. The reactor may be stirred internally or externally.

The amount of product produced in a reaction can be measured in various ways, for example, by enzymatic assays which produce a colored or fluorometric product or by high-performance liquid chromatography (HPLC) methods. In certain embodiments, the product is measured utilizing an assay which measures the activity or concentration of the particular product being produced.

Pathways of Interest

As used herein, the term "enzyme pathway" or "pathway of interest" refers to a cellular or acellular (cell-free) system for converting a substrate to a product of interest, where the system comprises a plurality of enzymes and may additionally comprise substrates acted upon by one or more of the enzymes, products of the enzyme-catalyzed reactions, co-factors utilized by the enzymes, and the like. The system may be present in an intact cell, or in a lysate of a cell. Many metabolic pathways are known and have been described in microbial systems, and are accessible in public databases; see, e.g., Smolke, Ed., *The Metabolic Pathway Engineering Handbook: Tools and Applications*, CRC Press, New York (2009); Stephanopoulos, Nielsen, and Aristidou, Eds., *Metabolic Engineering: Principles and Methodology*, Academic Press, New York (1998); Greenberg, *Metabolic Pathways: Energetics, Tricarboxylic Acid Cycle, and Carbohydrates*, Academic Press, New York (1967); and D. M. Greenberg's multi-volume series entitled *Metabolic pathways*, Volumes 1-7, each of which is incorporated herein by reference.

Pathways of interest include, for example, pathways involved in carbohydrate, amino acid, nucleic acid, steroid, fatty acid, and natural product biosynthesis, and encompass the synthesis of various chemical compounds and materials, including, but not limited to:

a) antibiotics; e.g., actinomycin, bleomycin, rifamycin, chloramphenicol, carbapenems, tetracycline, lincomycin, erythromycin, streptomycin, cyclohexamide, puromycin, cycloserine, bacitracin, penicillin, cephalosporin, vancomycin, polymyxin, and gramicidin;

b) biosurfactants; e.g., rhamnolipids, sophorolipids, glycolipids, and lipopeptides;

c) biological fuels; e.g., bioethanol, biodiesel, and biobutanol;

d) amino acids; e.g., L-glutamate, L-lysine, L-phenylalanine, L-aspartic acid, L-isoleucine, L-valine, L-tryptophan, L-proline (hydroxyproline), L-threonine, L-methionine, L-tyrosine, and D-p-hydroxyphenylglycine;

e) organic acids; e.g., citric acid, lactic acid, gluconic acid, acetic acid, propionic acid, succinic acid, fumaric acid, and itaconic acid;

f) fatty acids; e.g., arachidonic acid, polyunsaturated fatty acid (PUBA), and α-linoleic acid;

g) alcohols and polyols; e.g., glycerol, mannitol, erythritol, xylitol, poly-3-hydroxybutyrate, isobutanol, and 1-butanol;

h) flavors and fragrances; e.g., vanillin, benzaldehyde, dihydroxyacetone, 4-(R)-decanolide, and 2-actyl-1-pyrroline;

i) nucleotides; e.g., 5'-guanylic acid and 5'-inosinic acid;

j) vitamins; e.g., vitamin C, vitamin F, vitamin B2, provitamin D2, vitamin B12, folic acid, nicotinamide, biotin, 2-keto-L-gulonic acid, and provitamin Q10;

k) pigments; e.g., astaxanthin, β-carotene, leucopene, monascorubrin, and rubropunctatin;

l) sugars and polysaccharides; e.g., ribose, sorbose, xanthan, gellan, and dextran; and m) biopolymers and plastics; e.g., polyhydroxyalkanoates (PHA), poly-γ-glutamic acid, and 1,3-propanediol.

Other examples of pathways of interest include the synthesis of various *E. coli* metabolites. A "metabolite" is any substance used or produced during metabolism (e.g., an enzyme, substrate, or product). Herein, a metabolite is often, although not always, the product of an enzyme in the pathway of interest. Exemplary *E. coli* metabolites include, but are not limited to, 2,3-dihydroxybenzoic acid, 2-ketoglutarate, 3-phosphoglycerate, 4-hydroxybenzoate, 6-phosphogluconate, acetoacetyl-CoA, acetyl-CoA, acetylphosphate, adenine, adenosine, adenosine phosphosulfate, ADP, ADP-glucose, Alanine, AMP, anthranilate, arginine, Asparagine, Aspartate, ATP, carbamylaspartate, cis-aconitate, citrate, citrulline, CMP, coenzyme A, CTP, cyclic AMP, cytidine, cytosine, dAMP, dATP, dCTP, deoxyadenosine, deoxyguanosine, deoxyribose-5-P, dGMP, dihydroorotate, dihydroxyacetone phosphate, dTDP, dTTP, erythrose-4-phosphate, FAD, flavin mononucleotide, fructose-1,6-bisphosphate, fructose-6-phosphate, fumarate, GDP, gluconate, gluconolactone, glucosamine-6-phosphate, glucose-6-phosphate, glucose-1-phosphate, glutamate, glutamine, glutathione, glutathione disulfide, glyceraldehyde-3-phosphate, glycerate, glycerol-3-phosphate, GMP, GTP, guanine, guanosine, histidine, histidinol, homocysteine, inosine diphosphate, inosine monophosphate, inosine triphosphate, isoleucine, lysine, malate, malonyl-CoA, methionine, myo-inositol, N-Acetyl-glucosamine-1P, N-acetyl-ornithine, NAD+, NADH, NADP+, NADPH, ornithine, oxaloacetate, phenylalanine, phenylpyruvate, phosphoenolpyruvate, proline, propionyl-CoA, PRPP, pyruvate, quinolinate, riboflavin, ribose-5-phosphate, ribulose-5-phosphate, S-adenosyl-L-methionine, serine, shikimic acid, shikimate, succinate, succinyl-CoA, threonine, tryptophan, tyrosine, UDP, UDP-glucose, UDP-glucuronate, UDP-N-acetylglucosamine, uridine, UTP, valine, and xylulose-5-phosphate.

In certain embodiments, the pathway of interest provides for the synthesis of shikimic acid and/or shikimate (shikimate is the anionic form of shikimic acid) and synthetic intermediates thereto, an isoprenoid or terpene (e.g., amorphadiene, farnesene, lycopene, astaxanthin, vitamin A, menthol, beta-carotene), poly-3-hydroxybutyrate, isobutanol, and 1-butanol.

A number of reactions may be catalyzed by enzymes in a pathway of interest. Broad classes of enzymes, which can be identified by enzyme classification number, provided in parentheses, include, but are not limited to:

(EC 1) oxidoreductases; e.g., dehydrogenases, oxidases, reductases, oxidoreductases, synthases, oxygenases, monooxygenases, dioxygenases, lipoxygenases, hydrogenases, transhydrogenases, peroxidases, catalases, epoxidases, hydroxylases, demethylases, desaturases, dismutases, hydroxyltransferases, dehalogenases, and deiodinases;

(EC2) transferases; e.g., transaminases, kinases, dikinases, methyltransferases, hydroxymethyltransferases, formyltransferases, formiminotransferases, carboxytransferases, carbamoyltransferases, amidinotransferases, transaldolases, transketolases, acetyltransferases, acyltransferases palmitoyltransferases, succinyltransferases, malonyltransferases, galloyltransferases, sinapoyltransferases, tigloyltransferases, tetradecanoyltransferases, hydroxycinnamoyltransferases, feruloyltransferases, mycolyltransferases, benzoyltransferases, piperoyltransferases, trimethyltridecanoyltransferase, myristoyltransferases, coumaroyltransferases, thiolases, aminoacyltransferases, phosphorylases, hexosyltransferases, pentosyltransferases, sialyltransferases, pyridinylases, diphosphorylases, cyclotransferases, sulfurylases, adenosyltransferases, carboxyvinyltransferases, isopentenyltransferases, aminocarboxypropyltransferases, dimethylallyltransferases, farnesyltranstransferases, hexaprenyltranstransferases, decaprenylcistransferases, pentaprenyltranstransferases, nonaprenyltransferases, geranylgeranyltransferases, aminocarboxypropyltransferases, oximinotransferases, purinetransferases, phosphodismutases, phosphotransferases, nucleotidyltransferases, polymerases, cholinephosphotransferases, phosphorylmutases, sulfurtransferases, sulfotransferases, and CoA-transferases;

(EC3) hydrolases; e.g., lipases, esterases, amylases, peptidases, hydrolases, lactonases, deacylases, deacetylases, pheophorbidases, depolymerases, thiolesterases, phosphatases, diphosphatases, triphosphatases, nucleotidases, phytases, phosphodiesterases, phospholipases, sulfatases, cyclases, oligonucleotidases, ribonucleases, exonucleases, endonucleases, glycosidases, nucleosidases, glycosylases, aminopeptidases, dipeptidases, carboxypeptidases, metallocarboxypeptidases, omega-peptidases, serine endopeptidases, cystein endopeptidases, aspartic endopeptidases, metalloendopeptidases, threonine endopeptidases, aminases, amidases, desuccinylases, deformylases, acylases, deiminases, deaminases, dihydrolases, cyclohydrolases, nitrilases, ATPases, GTPases, halidases, dehalogenases, and sulfohydrolases;

(EC 4) lyases; e.g., decarboxylases, carboxylases, carboxykinases, aldolases, epoxylyases, oxoacid-lyases, carbon-carbon lyases, dehydratases, hydratases, synthases, endolyases, exolyases, ammonia-lyases, amidine-lyases, amine-lyases, carbon-sulfur lyases, carbon-halide lyases, phosphorus-oxygen lyases, and dehydrochlorinases;

(EC 5) isomerases; e.g., isomerases, racemases, mutases, tautomerases, phosphomutases, phosphoglucomutases, aminomutases, cycloisomerase, cyclases, topoisomerases; and (EC 6) ligases; e.g., synthetases, tNRA-ligases, acid-thiol ligases, amide synthases, peptide synthases, cycloligases, carboxylases, DNA-ligases, RNA-ligases, and cyclases.

More specific classes of enzymes include, without limitation, sub-classes of oxidoreductases, transferases, lyases, isomerases, and ligases, as provided below.

Exemplary oxidoreductases include, but are not limited to:

(EC 1.1) oxidoreductases acting on the CH—OH group of donors, and an acceptor;

(EC 1.2) oxidoreductases acting on the aldehyde or oxo group of donors, and an acceptor;

(EC 1.3) oxidoreductases acting on the CH—CH group of donors, and an acceptor;

(EC 1.4) oxidoreductases acting on the CH—NH2 group of donors, and an acceptor;

(EC 1.5) oxidoreductases acting on the CH—NH group of donors, and an acceptor;

(EC 1.6) oxidoreductases acting on NADH or NADPH, and an acceptor;

(EC 1.7) oxidoreductases acting on other nitrogenous compounds as donors, and an acceptor;

(EC 1.8) oxidoreductases acting on a sulfur group of donors, and an acceptor;

(EC 1.9) oxidoreductases acting on a heme group of donors, and an acceptor;

(EC 1.1) oxidoreductases acting on diphenols and related substances as donors, and an acceptor;

(EC 1.11) oxidoreductases acting on a peroxide as acceptor;

(EC 1.12) oxidoreductases acting on hydrogen as donor, and an acceptor;

(EC 1.13) oxidoreductases acting on single donors with incorporation of molecular oxygen, incorporating one or two oxygen atoms;

(EC 1.14) oxidoreductases acting on paired donors, with incorporation or reduction of molecular oxygen, with the donor being 2-oxoglutarate, NADH, NADPH, reduced flavin, flavoprotein, pteridine, iron-sulfur protein, ascorbate;

(EC 1.15) oxidoreductases acting on superoxide radicals as acceptor;

(EC 1.16) oxidoreductases oxidizing metal ions, and an acceptor;

(EC 1.17) oxidoreductases acting on CH or CH2 groups, and an acceptor;

(EC 1.18) oxidoreductases acting on iron-sulfur proteins as donors, and an acceptor;

(EC 1.19) oxidoreductases acting on reduced flavodoxin as donor, and an acceptor;

(EC 1.2) oxidoreductases acting on phosphorus or arsenic in donors, and an acceptor; and (EC 1.21) oxidoreductases acting on X—H and Y—H to form an X—Y bond, and an acceptor; where acceptors for each donor category may include, without limitation: NAD, NADP, heme protein, oxygen, disulfide, quinone, an iron-sulfur protein, a flavin, a nitrogenous group, a cytochrome, dinitrogen, and H+.

Exemplary transferases include, but are not limited to:
(EC 2.1) transferases transferring one-carbon groups;
(EC 2.2) transferases transferring aldehyde or ketonic groups;
(EC 2.3) Acyltransferases;
(EC 2.4) Glycosyltransferases;
(EC 2.5) transferases transferring alkyl or aryl groups, other than methyl groups;
(EC 2.6) transferases transferring nitrogenous groups;
(EC 2.7) transferases transferring phosphorus-containing groups;
(EC 2.8) transferases transferring sulfur-containing groups; and
(EC 2.9) transferases transferring selenium-containing groups.

Exemplary hydrolases include, but are not limited to:
(EC 3.1) hydrolases acting on ester bonds;
(EC 3.2) Glycosylases;
(EC 3.3) hydrolases acting on ether bonds;
(EC 3.4) hydrolases acting on peptide bonds (peptidases);
(EC 3.5) hydrolases acting on carbon-nitrogen bonds, other than peptide bonds;
(EC 3.6) hydrolases acting on acid anhydrides;
(EC 3.7) hydrolases acting on carbon-carbon bonds;
(EC 3.8) hydrolases acting on halide bonds;
(EC 3.9) hydrolases acting on phosphorus-nitrogen bonds;
(EC 3.1) hydrolases acting on sulfur-nitrogen bonds;
(EC 3.11) hydrolases acting on carbon-phosphorus bonds;
(EC 3.12) hydrolases acting on sulfur-sulfur bonds; and
(EC 3.13) hydrolases acting on carbon-sulfur bonds.

Exemplary lyases include, but are not limited to:
(EC 4.1) Carbon-carbon lyases;
(EC 4.2) Carbon-oxygen lyases;
(EC 4.3) Carbon-nitrogen lyases;
(EC 4.4) Carbon-sulfur lyases;
(EC 4.5) Carbon-halide lyases; and
(EC 4.6) Phosphorus-oxygen lyases.

Exemplary isomerases include, but are not limited to:
(EC 5.1) Racemases and epimerases;
(EC 5.2) cis-trans-Isomerases;
(EC 5.3) Intramolecular isomerases;
(EC 5.4) Intramolecular transferases (mutases); and
(EC 5.5) Intramolecular lyases.

Exemplary ligases include, but are not limited to:
(EC 6.1) ligases forming carbon-oxygen bonds;
(EC 6.2) ligases forming carbon-sulfur bonds;
(EC 6.3) ligases forming carbon-nitrogen bonds;
(EC 6.4) ligases forming carbon-carbon bonds;
(EC 6.5) ligases forming phosphoric ester bonds; and
(EC 6.6) ligases forming nitrogen-metal bonds.

Isozymes (also known as isoenzymes) are enzymes that differ in amino acid sequence but catalyze the same chemical reaction. At some points in a pathway of interest, two or more isozymes may be present. Isozymes may display different kinetic parameters, and/or different regulatory properties.

Enzymes involved in a pathway of interest or associated pathway may also be classified according to the role of the enzyme. Direct involvement enzymes (class 1) in a cell or cell lysate catalyze a reaction in the pathway. It is typical of pathways that such direct enzymes are one of a chain, where a product of a first enzyme is the substrate of a second enzyme, the product of the second enzyme is the substrate of a third enzyme, and so forth, which eventually results in the product of interest. Indirect involvement enzymes (class 2) in a cell or cell lysate react in an associated pathway, usually in the production of a substrate used in the pathway of interest.

Within a pathway, enzymes will vary in turnover rate and the effectiveness with which a product is produced. As a result, certain enzymes in a pathway become rate-limiting. Increasing the concentration of rate-limiting enzymes in a pathway (relative to non-rate limiting enzymes) allows increased flux through the pathway of interest (see, e.g., Zamboni et al. *Nature Protocols* (2009) 4:878-892, incorporated herein by reference). Often rate-limiting enzymes are associated with toxicity when over-produced, and thus the available concentrations of such enzymes is desirably modulated. See, e.g., PCT Publication No. WO 2010/077806, incorporated herein by reference.

A third class of enzymes in a cell or cell lysate are competing enzymes (class 3), which utilize a substrate or product of the pathway of interest. A characteristic of a competing enzyme is that the kinetics of the substrate conversion are sufficiently high that the presence of the enzyme decreases the overall yield and/or the rate of production of the desired final product catalyzed by the pathway of interest. A normal cell may require the expression of competing enzymes, and therefore rather than knocking out expression of competing enzymes completely, it is desirable to selectively decrease the concentration of the active enzyme by the methods described herein.

For convenience of naming, an enzyme in the pathway may be categorized as a first, pathway entry enzyme, or a subsequent downstream enzyme or enzymes. For convenience, the pathway entry enzyme may be referred to herein as $E_1$, and the downstream enzymes may be consecutively numbered, $E_2, E_3, \ldots E_n$. Pathways of interest for use in the methods of the described herein will usually comprise at least one enzyme, at least two enzymes, at least three enzymes, at least four enzymes, or more, e.g., between 1 to 50 enzymes, between 1 to 40 enzymes, between 1 to 30 enzymes, between 1 to 20 enzymes, between 1 to 10 enzymes, between 1 to 5 enzymes, between 1 to 2 enzymes, between 2 to 50 enzymes, between 2 to 40 enzymes, between 2 to 30 enzymes, between 2 to 20 enzymes, between 2 to 10 enzymes, between 2 to 5 enzymes, between 2 to 4 enzymes, between 5 to 50 enzymes, between 5 to 40 enzymes, between 5 to 30 enzymes, between 5 to 20 enzymes, between 5 to 10 enzymes, between 5 to 8 enzymes, between 10 to 50 enzymes, between 10 to 40 enzymes, between 10 to 30 enzymes, or between 10 to 20 enzymes, inclusive.

Enzymes in a pathway may be naturally occurring, or modified to optimize a particular characteristic of interest, e.g., substrate specificity, reaction kinetics, solubility, and/or insensitivity to feedback inhibition. In addition, in some cases, the gene expressing the enzyme will be optimized for codon usage within the host cell. In some embodiments, the complete pathway comprises enzymes from a single organism, however such is not required, and combining enzymes from multiple organisms is also contemplated. For some purposes, a pathway may be endogenous to the host cell, but such is also not required, and a complete pathway or components of a pathway may be introduced into a host cell. Where the system is provided in an intact cell, the complete set of enzymes of the pathway of interest can be present in the cell. For purposes of cell-free production, one or more enzymes may be added to the lysate, or alternatively may be produced by the lysate, so as to complete the pathway. The enzyme may be isolated and/or purified.

In the pathway system, a first substrate ($S_1$) is acted upon by the pathway entry enzyme, and is converted to a first product, although it will be understood by one of skill in the art that an enzyme may act upon more than one substrate simultaneously, and may produce more than one product, such that two or more pathways may be interconnected at a single enzyme. The first product is a substrate ($S_2$) for downstream enzyme $E_2$, and is converted to a second product by $E_2$. Depending on the complexity of the pathway, the second product may be the final product (PF), or may be a substrate ($S_3$) for a third downstream enzyme ($E_3$), and is converted to a third product by $E_3$, which may be a substrate ($S_4$) for a fourth enzyme. The final enzyme in the pathway, which may be, for example, $E_2$, $E_3$, or $E_4$, produces the product of interest (PF). It is a characteristic of enzymatic pathways that the product of one enzyme is the substrate for the next enzyme.

Products may be stable or relatively labile, but in some instances the final product is sufficiently stable that it can be isolated from the cell, cell lysate, or reaction mixture. Competing enzymes utilize a substrate or product of the pathway of interest, which may include any one of PF, $S_1$, $S_2$, $S_3$, and/or $S_4$, and may be referred to as competing enzymes ($E_C$).

In some embodiments, the initial substrate, $S_1$, is a central metabolite, or cellular "commodity". The central pathways of metabolism include glycolysis and the citric acid cycle. Such $S_1$ compounds may not be specific to the pathway of interest, but are compounds widely found in various cells and are substrates for multiple enzymes and pathways. Examples of commodity substrates include, without limitation, glucose, ATP, pyruvate, phosphoenol pyruvate, and the like. A pathway entry enzyme, $E_1$, may convert a commodity substrate to a product that is a selective substrate for one or a relatively small number of enzymes. In some embodiments, $S_1$ compounds or cellular commodities are added to the cell lysate.

In some embodiments, a key entry enzyme is defined as one that performs the first committed step in a pathway to a product of interest. This step may involve the biochemical commitment of a compound to the pathway of a product of interest. Examples of key entry enzymes include, but are not limited to, those set forth in Table 1.

TABLE 1

Exemplary list of key pathway entry enzymes

| Key Entry Enzyme(s) | Biosynthetic Pathway | Example Products | E. coli enzyme |
| --- | --- | --- | --- |
| amidophosphoribosyl transferase | purine biosynthesis | GMP, GDP, GTP, dGDP, dGTP, AMP, ADP, ATP, dADP, dATP, inosine monophosphate | PurF |
| orotate phosphoribosyltransferase | pyrimidine biosynthesis | UMP, UDP, UTP, CDP, CTP | PyrE |
| 2-dehydro-3-deoxyphosphoheptonate aldolase | chorismate biosynthesis | Shikimate, Tyrosine, Phenylalanine, Tryptophan | AroE, F, G |
| phosphoribosyltransferase HisG | histidine biosynthesis | Histidine | HisG |
| acetolactate/acetohydroxybutanoate synthase | isoleucine, leucine, valine biosynthesis | Isoleucine, Leucine, Valine | IlvH, M, N |
| UDP-N-acetylglucosamine acyltransferase | lipopolysaccharide biosynthesis | Lipid A disaccharide | LpxA |
| aspartate aminotransferase | lysine, threonine and methionine biosynthesis | Lysine, Threonine, Methionine | AspC |
| arginine decarboxylase | putrescine biosynthesis | Putrescine | SpeA |
| GTP cyclohydrolase I | tetrahydrofolate biosynthesis | Tetrahydrofolate | FolE |
| acetyl-CoA carboxylase | fatty acid biosynthesis | Malonyl-CoA | AccA, B, C, D |

A specific non-limiting example of a pathway, provided for illustrative purposes, is the pathway for the synthesis of shikimic acid. In this pathway, for example, a reaction between the cellular commodity compounds phosphoenolpyruvate ($S_{1A}$) and erythrose-4-phosphate ($S_{1B}$) is catalyzed by the enzyme DAHP synthase ($E_1$) to form 3-deoxy-D-arabinoseheptulose-7-phosphate (DAHP). DAHP($S_2$) is transformed to 3-dehydroquinate (3-DHQ) by the second enzyme in the pathway, DHQ synthase ($E_2$). 3-DHQ ($S_3$) is dehydrated to 3-dehydroshikimate by the third enzyme in the pathway, 3-DHQ dehydratase ($E_3$). 3-dehydroshikimate ($S_4$) is reduced to shikimic acid (PF) by the fourth enzyme in the pathway, shikimate dehydrogenase (E₄), using NADPH as a cofactor. The enzymes of the pathway are known in the art and have been characterized in a number of organisms, including, for example, *E. coli*, in which the enzymes are encoded by the genetic loci as follows: DAHP synthase (aroG, aroF, aroH); DHQ synthase (aroB); 3-DHQ dehydratase (aroD); shikimate dehydrogenase (aroE); see, e.g., PCT Publication No. WO2010/074760, incorporated herein by reference.

Metabolic Flux

"Flux" or "metabolic flux" refers to the rate that molecules pass through a pathway or reaction of interest. Among the factors that control flux are rate of catalysis of enzymes in the pathway, the availability of substrate, the concentration of enzymes in a cell, and/or the proximity of enzymes in a pathway.

those of skill in the art, and include, without limitation, tobacco etch virus protease (ENLYFQ$^{G/S}$) (SEQ ID NO:20); yellow fever virus protease (GARR$^{G/S}$) (SEQ ID NO:21); thrombin (LVPRGS) (SEQ ID NO:22); and Factor Xa (I$^{E/D}$GR) (SEQ ID NO:23).

In certain embodiments, described herein are methods of generating site-specific proteases having a periplasmic relocation sequence. Synthesis of genes coding for each site-specific protease enables codon optimization for expression in *E. coli* cells. Polymerase chain reaction (PCR), or other methods familiar to those skilled in the art, can be used for the addition of the periplasmic relocation sequence. Genes are sub-cloned into vectors enabling controlled expression (e.g., vectors enabling controlled expression using the T7 induction system, such as a vector from the pET series).

TABLE 2

Examples of specific proteases

| Name | MEROPS | UniProt | | Specific Site |
|---|---|---|---|---|
| TEV NIa | C04.004 | P04517 | (2036-2279) | E-N-L-Y-F-Q↓G (SEQ ID NO: 12) |
| HRV 3C | C03.007 | P04936 | (1508-1690) | L-E-V-L-F-Q↓G-P (SEQ ID NO: 13) |
| Enterokinase | S01.156 | P98072 | (801-1035) bovine | D-D-D-D-K↓ (SEQ ID NO: 14) |
| Factor Xa | S01.216 | P00743 | (234-468) bovine | I-E-G-R↓ (SEQ ID NO: 15) |
| Thrombin (fIIa) | S01.217 | P00735 | (367-623) bovine | L-V-P-R↓G (SEQ ID NO: 16) |

While a high rate of flux through a pathway of interest is desirable, at the same time it can create toxicity issues if a product not normally accumulated at high levels in the cell is produced at a high rate relative to that occurring under normal conditions. It is understood that a high rate of flux is pathway specific, and refers to the concentration of pathway product over time, such as, for example, production of a product at a rate of about 0.1 grams (g) to about 20 g of product/L/h. In some embodiments, the rate of product production is about 0.5, about 1, about 2, about 5, about 10, or about 15 grams of product/L/h.

Methods of determining flux rates are known and used in the art; see, e.g., Wiechert et al., *Metab. Eng.* (2001) 3:265-283; Wiechert et al., *Metab. Eng.* (2001)3:195-206; and metabolic engineering texts such as Lee and Papoutsakis, Eds., *Metabolic Engineering*, Marcel Dekker, Inc. New York (1999); Stephanopoulos, Nielsen, and Aristidou, Eds., *Metabolic Engineering: Principles and Methodology*, Academic Press, New York (1998); and Nielsen and Eggeling, Eds., *Metabolic Engineering*, Springer, London (2001), each of which is incorporated herein by reference. Flux may be calculated from measurable quantities using techniques such as metabolic flux analysis (MFA), for example, by direct measurement of the conversion rate of isotopically labeled substrate.

Site-Specific Protease

As used herein, the term refers to a protease, for example, an endoprotease, which cleaves selectively at a specific amino acid motif. In some embodiments, the amino acid motif is a motif of at least 4 amino acid residues to reduce background protein cleavage, and may be a motif of at least 5 amino acids, at least 6 amino acids, or more. Such proteases are known to In certain embodiments, a site-specific protease coding sequence is introduced into the microbial cell. The site-specific protease coding sequence may be operably linked to a constitutive or regulatable promoter, e.g., an inducible promoter, which may be referred to herein as a site-specific protease expression construct. The site-specific protease expression construct may be provided on an episomal vector, e.g., a plasmid, YAC, BAC, or viral vector, as known in the art. Alternatively, the site-specific protease expression construct may be integrated into the chromosome of the microbial host cell.

In some embodiments, the expression rate of the site-specific protease is experimentally adjusted to optimize efficiency of export of the protease out of the cell or into the periplasm of the cell. Poor translocation can result from insufficient capacity of export machinery. Methods for adjustment of expression rate include, without limitation, modification of copy number of the plasmid carrying the gene coding for the site-specific protease to be exported to the periplasm. Replicons known and used in the art include P15A (10 copies/cell), ColA (30 copies/cell), ColE1 (40 copies/cell), and RSF1030 (>100 copies/cell). The ribosome binding site in the 5' UTR of the gene coding for the site-specific protease to be exported to the periplasm may be modified, where a library of ribosome binding sites with varying strengths can be created and tested for use in the embodiments described herein, see *Nature Biotechnology* 27: 946-950, 2009; *Nature Biotechnology* 14:629, 1996, each herein specifically incorporated by reference. The promoter region upstream of the gene coding for the protein, e.g., a site-specific protease, to be exported may be modified to adjust the rate of transcription, where a library of promoter regions with varying strengths can be created and tested for use in the embodiments described herein, see PNAS 102:12678-12683, 2005; *BMC Biotechnology* 7:34, 2007, each herein specifically incorporated by reference.

Protease Cleavage Site

As described above, a site-specific protease cleaves targeted enzymes in a sequence-specific manner, e.g., at ENLYFQ$^{G/S}$ (SEQ ID NO:20), GARR$^{G/s}$ (SEQ ID NO:21), LVPRGS (SEQ ID NO:22), or I$^{E/D}$GR (SEQ ID NO:23). The methods described herein may utilize, in part, a modification of targeted genetic sequences to make a targeted enzyme labile to site-specific protease digestion and consequent inactivation. In addition, the site-specific protease may be selected such that the pathway enzymes of interest are not cleaved by the protease.

The enzyme targeted for site-specific protease cleavage may be an enzyme that competes with an enzyme in the pathway of interest, e.g., an enzyme that utilizes a substrate or product of the pathway and by so doing reduces flux through the pathway or reduces production of the desired product. The targeted enzyme may be altered by amino acid insertion or substitution to generate a site-specific protease cleavage site, for example, by a neutral substitution with conservative or no amino acid changes. By "neutral substitution" it is intended that the amino acid at a position within the motif (e.g., site-specific protease recognition site) is substituted with an amino acid that maintains the targeted enzyme's activity. Such an amino acid sequence may be referred to as "protease labile sequence." In certain embodiments, the site for cleavage is selected such that, following cleavage, the targeted enzyme's activity is destroyed. In some embodiments, the enzyme's activity is not completely destroyed (e.g., 100% inactive, or reduced by 100%), but rather is reduced by 99%, about 90%, about 80%, about 70%, about 60%, or about 50%. In some embodiments, a targeted enzyme is considered to be inactive if the level of enzymatic activity is such that the targeted enzyme is not capable of competing with enzymes in the pathway of interest.

A targeted enzyme may be selected by pathway analysis to identify enzymes that divert/decelerate flux away from the product of interest or that catalyze a side reaction that siphons flux from a product of interest. It may first be determined whether these enzyme activities can be removed from the host strain (e.g., through genomic knockout) without adversely affecting cell growth. In cases where complete removal of enzyme activity would substantially harm or otherwise negatively affect the metabolic health of the host, the enzyme(s) performing this activity are targeted for degradation by a relocated site-specific protease. In this way, flux to the product of interest may be increased.

In some embodiments, a library of targeted enzyme sequences with protease cleavage sites inserted at varying positions is initially created to determine the optimal site-specific recognition site and/or placement of the site. Positions may be chosen based on the structure (e.g., tertiary structure) of the targeted enzyme, for example, by inserting the site-specific recognition site in surface-exposed loop regions. Where structural information for the targeted enzyme is not available, the positioning of the recognition site may be determined by comparing amino acid sequences of targeted enzyme homologs and identifying hydrophilic regions with high sequence and length variability. Hydrophilic residues are commonly exposed on the enzyme surface, and high sequence and length variability can indicate that the region is not critical for enzyme function and can tolerate sequence modification. For example, see *Journal of Virology* 78:5079, 2004; U.S. Pat. No. 7,223,390, herein incorporated by reference, which teach that limited proteolytic digestion followed by chromatographic co-fractionation and N-terminal polypeptide sequencing/mass spectroscopy can be used to determine such candidate sites which are accessible to protease digestion and nonessential for forming an integral enzyme/protein structure.

Modification of an amino acid sequence of the targeted enzyme to introduce a site-specific recognition site may be accomplished by methods of gene engineering known in the art, for example using PCR-based and ligation-based methods, or by methods of genomic modification known to those skilled in the art. See, for example Phusion site-directed mutagenesis kit (New England Biolabs); *Journal of Virological Methods* 149:85, 2008; *Nucleic Acids Research* 32:e174, 2004; *Journal of Bacteriology* 180: 2063, 1998; *Proceedings of the National Academy of Sciences of the United States of America* 97:6640, 2000, each herein specifically incorporated by reference.

Periplasmic Sequestration

In some embodiments, site-specific protease relocation is to the periplasmic space of the cell. In such aspects, described herein are methods of generating cells, lysates, and uses thereof, whereby a protease is genetically modified to incorporate a peptide relocation sequence that provides for periplasmic targeting of the protease. Periplasmic relocation sequences (also referred to herein as targeting peptide sequences, targeting signals, signal peptides, or signal sequences), in some embodiments, are found at the N-terminus of bacterial secretory proteins. They vary in length from about 15 to about 70 amino acids. The primary sequences of amino acids also vary, but may have a common overall structure, including the following parts: (i) an N-terminal part having a variable length and carrying, for example, a net positive charge; (ii) a central hydrophobic core of about 6 to about 15 amino acids; and (iii) about 4 to about 6 amino acids defining the cleavage site for signal peptidases.

Periplasmic relocation sequences suitable for use herein may be derived from a protein that is secreted in a Gram negative bacterium. The secreted protein may be encoded by the bacterium or by a bacteriophage that infects the bacterium. Examples of suitable Gram negative bacterial sources of secreted proteins include but are not limited to, members of the genera *Escherichia, Pseudomonas, Klebsiella, Salmonella, Caulobacter, Methylomonas, Acetobacter, Achromobacter, Acinetobacter, Aeromonas, Agrobacterium, Alcaligenes, Azotobacter, Burkholderia, Citrobacter, Comamonas, Enterobacter, Erwinia, Rhizobium, Vibrio,* and *Xanthomonas*.

There are three pathways for translocation of proteins across cytoplasmic membranes: (i) SecB-dependent, (ii) signal recognition particle (SRP), and (iii) twin arginine translocation (TAT) pathways. SecB-dependent and signal recognition particle pathways both use the SecYEG translocon. The twin arginine translocation pathway uses the TatABCE complex. SecB-dependent translocation is most commonly used, but this pathway is not able to transport folded proteins. Rapid cytoplasmic folding may necessitate use of TAT pathway. Examples of bacterial secreted proteins having periplasmic relocation sequences include, but are not limited to, proteins encoded by the following genes: ompA, geneIII, *E. coli* alkaline phosphatase, lamB, malE, secE, secY, and prlA-4. One skilled in the art can identify the periplasmic relocation sequence located at the N-terminus of each of these proteins and other bacterial secretory proteins. It is also known by one skilled in the art that some amino acid substitutions, additions, and/or deletions may be made in a periplasmic relocation sequences while retaining the periplasmic targeting function. Thus, a functional periplasmic relocation sequence as described herein may be a fully natural or a modified sequence.

In some embodiments, the site-specific protease is relocated to an extracytoplasmic location. Signals for secretion in bacterial cells are known in the art, for example, sec and Tat translocons in *B. subtilis* (see for review Buist et al. (2006) *Microbiology* 152(Pt 10):2867-74; and Tjalsma et al. (2004) *Microbiol Mol Biol Rev.* 68(2):207-33), each herein specifically incorporated by reference. ClyA export from bacterial cells is also known in the art, for example see Ludwig et al. (2010) *J Bacteriol.* 192(15):4001-11, herein incorporated by reference.

In other embodiments, the site-specific protease is relocated to a nuclear compartment. Peptide signals for nuclear relocation are known in the art, for example the SV40 large T-cell antigen peptide: PKKKRKV (SEQ ID NO: 24) (see Kalderon et al. (1984) Cell 39 (3 Pt 2): 499-509); and the nucleoplasmin peptide: KR[PAATKKAGQA]KKKK (SEQ ID NO:25) (see Dingwall et al. (1988) *J Cell Biol.* 107 (3): 841-9). In other embodiments, localization may be made to the thylakoid membrane, see, for example Schnell (1998) *Annual Review of Plant Physiology and Plant Molecular Biology* Vol. 49: 97-126; Ko and Cashmore (1989) *EMBO J.* 8(11): 3187-3194; de Boer et al. (1991) *EMBO J.* 10(10): 2765-2772; and Mackle and Zilinskas (1994) *J. Bacteriol.* 176(7):1857-1864; each herein specifically incorporated by reference.

Fusion proteins described herein may comprise a periplasmic relocation sequence and/or a site-specific protease. In certain embodiments, the optimal periplasmic relocation sequence for the site-specific protease is empirically determined from a selection of such sequences. The efficiency of secretion of the site-specific protease may depend on various parameters, including the relocation sequence, the protease being relocated, host cell strain used, protease expression level, and other parameters. For example, a library of modified genes with varying 5' regions coding for different periplasmic relocation sequences can be created using PCR or other methods known to those skilled in the art. This library is subcloned in a vector enabling controlled expression (e.g., a vector enabling controlled expression using the T7 induction system such as a vector from the pET series), and tested for export efficiency as well as protein activity (see J. Biol. Chem. 267:4882, 1992; J. Biol. Chem. 267:12375, 1992; US2007/0111283 A1; and Biotechnology Advances 23:177, 2005, each herein specifically incorporated by reference).

Examples of periplasmic relocation sequences include, without limitation:

TABLE 3

Examples of periplasmic relocation sequences

| Name | Signal peptide | kDa | Pathway | Source |
|------|----------------|-----|---------|--------|
| MalE | MKIKTGARILALSALTTMM FSASALA (SEQ ID NO: 1) | 2.7 | Sec | *E. coli* |
| OmpA | MKKTAIAIAVALAGFATVA QA (SEQ ID NO: 2) | 2.0 |  | *E. coli* |
| PhoA | MKQSTIALALLLPLLFTPVT KA (SEQ ID NO: 3) | 2.3 | Sec | *E. coli* |

TABLE 3-continued

Examples of periplasmic relocation sequences

| Name | Signal peptide | kDa | Pathway | Source |
|------|----------------|-----|---------|--------|
| LamB | MMITLRKLPLAVAVAAGVM SAQAMA (SEQ ID NO: 4) | 2.6 | Sec | *E. coli* |
| MglB | MNKKVLTLSAVMASMLFGA AAHA (SEQ ID NO: 5) | 2.4 | Sec | *E. coli* |
| PelB | MKYLLPTAAAGLLLLAAQP AMA (SEQ ID NO: 6) | 2.2 | Sec | *E. caratovora* |
| STII | MKKNIAFLLASMFVFSIAT NAYA (SEQ ID NO: 7) | 2.6 |  | *E. coli* |
| DsbA | MKKIWLALAGLVLAFSASA (SEQ ID NO: 8) | 2.0 | SRP | *E. coli* |
| SfmC | MMTKIKLLMLIIFYLIISA SAHA (SEQ ID NO: 9) | 2.6 | SRP | *E. coli* |
| TolB | MKQALRVAFGFLILWASVL HA (SEQ ID NO: 10) | 2.4 | SRP | *E. coli* |
| TorT | MRVLLFLLLSLFMLPAFS (SEQ ID NO: 11) | 2.1 | SRP | *E. coli* |

A cleavage site is optionally located between the relocation sequence and the site-specific protease to allow separation. The cleavage site may be any site that can be used in separating the relocation sequence and the site-specific protease coding sequence. Any cleavage site making use of any method for protein cleavage may be used. Periplasmic relocation sequences from *E. coli* may contain within their signal sequence a motif recognized by leader peptidase, Lep, for signal sequence processing and cleavage. Other methods that have been successfully used and are well known to one skilled in the art include protease cleavage methods, e.g. thrombin, factor Xa protease and other endo peptidases, such as trypsin. The genes encoding the fusion protein can be synthesized to include a cleavage site for one of these proteases between the relocation sequence and the protease sequence. Another system for fusion and cleavage is the intein/chitin binding domain system (S. Chong, et al., *Gene*, Vol. 192, 271-281 (1997)). This system makes use of the self-cleaving properties of intein proteins.

Nucleic Acids, Polypeptides, and Cells

The nucleic acids used as described herein, whether RNA, iRNA (also known as RNAi), antisense nucleic acid, cDNA, genomic DNA, vectors, artificial chromosomes, viruses, or hybrids thereof may be isolated from a variety of sources, genetically engineered, amplified, and/or expressed/generated recombinantly. A nucleic acid molecule or nucleic acid molecules that encode any of the targeted enzymes or site-specific proteases associated with the embodiments described herein can be introduced into a cell or cells using methods and techniques that are known in the art. For example, nucleic acid molecules can be introduced into cells by standard protocols such as transformation, including chemical transformation and electroporation, transduction, and particle bombardment. Expressing a nucleic acid molecule(s) encoding a targeted enzyme or site-specific protease may also be accomplished by integrating the nucleic acid molecule into the genome of the cell. Nucleic acid molecule(s) can be integrated into a cell's genomic DNA using standard techniques known in the art. Recombinant polypeptides generated from these nucleic acids can be individually isolated or cloned and tested for a desired activity. "Polypeptide" and "protein," as used herein, encompasses targeted enzymes and site-specific proteases. Any recombinant expression system can be used, including, but not limited to, bacterial, mammalian, yeast, insect, or plant cell expression systems. The nucleic acids used as described herein can be synthesized in vitro by well-known chemical synthesis techniques, as described in, e.g., Adams et al., *J. Am. Chem. Soc.* (1983) 105:661; Belousov et al., *Nucleic Acids Res.* (1997) 25:3440-3444; Frenkel et al., *Free Radic. Biol. Med.* (1995) 19:373-380; Blommers et al., *Biochemistry* (1994) 33:7886-7896; Narang et al., *Meth. Enzymol.* (1979) 68:90; Brown et al., *Meth. Enzymol.* (1979) 68:109; Beaucage et al., *Tetrahedron Letters* (1981) 22:1859; and U.S. Pat. No. 4,458,066, each of which is incorporated herein by reference.

Host cells for pathway engineering include a wide variety of heterotrophic and autotrophic microorganisms, including, but not limited to, bacteria, fungi and protozoans. In certain embodiments, host cells include those for which means by which a polypeptide can be directed to a cellular compartment or extracellular compartments are known. In some embodiments, the cell is any type of cell that recombinantly expresses any one or more of the nucleic acids (e.g., site-specific protease or targeted enzyme coding sequences) described herein. Such cells include prokaryotic and eukaryotic cells. In some embodiments, the cell is a bacterial cell, such as *Escherichia* spp., *Streptomyces* spp., *Zymonas* spp., *Acetobacter* spp., *Citrobacter* spp., *Synechocystis* spp., *Rhizobium* spp., *Clostridium* spp., *Corynebacterium* spp., *Streptococcus* spp., *Xanthomonas* spp., *Lactobacillus* spp., *Lactococcus* spp., *Bacillus* spp., *Alcaligenes* spp., *Pseudomonas* spp., *Aeromonas* spp., *Azotobacter* spp., *Comamonas* spp., *Mycobacterium* spp., *Rhodococcus* spp., *Gluconobacter* spp., *Ralstonia* spp., *Acidithiobacillus* spp., *Microlunatus* spp., *Geobacter* spp., *Geobacillus* spp., *Arthrobacter* spp., *Flavobacterium* spp., *Serratia* spp., *Saccharopolyspora* spp., *Thermus* spp., *Stenotrophomonas* spp., *Chromobacterium* spp., *Sinorhizobium* spp., *Saccharopolyspora* spp., *Agrobacterium* spp. and *Pantoea* spp. The bacterial cell can be a Gram-negative cell such as an *Escherichia coli* (*E. coli*) cell, or a Gram-positive cell such as a species of *Bacillus*. In other embodiments the cell is a fungal cell such as yeast cells, e.g., *Saccharomyces* spp., *Schizosaccharomyces* spp., *Pichia* spp., *Paffia* spp., *Kluyveromyces* spp., *Candida* spp., *Talaromyces* spp., *Brettanomyces* spp., *Pachysolen* spp., *Debaryomyces* spp., *Yarrowia* spp. and industrial polyploid yeast strains. Other non-limiting examples of fungi include *Aspergillus* spp., *Pennicilium* spp., *Fusarium* spp., *Rhizopus* spp., *Acremonium* spp., *Neurospora* spp., *Sordaria* spp., *Magnaporthe* spp., *Allomyces* spp., *Ustilago* spp., *Botrytis* spp., and *Trichoderma* spp. In other embodiments, the cell is an algal cell, a plant cell, or a mammalian cell. It should be appreciated that some cells compatible with the embodiments described herein may express an endogenous copy of one or more of the genes described herein as well as a recombinant copy. Species of interest include, without limitation, *S. cerevisiae, E. coli, Pseudomonas* species, *Klebsiella* species, and *Synechocystis* species. To avoid unwanted degradation of the relocated site-specific protease, the host strain can be modified to remove various compartmental proteases (e.g., periplasmic proteases) and/or to augment with proteins such as chaperones and maturases to assist with protein folding. Such modifications and augmentations employ methods known to those skilled in the art, see, e.g., U.S. Pat. Nos. 4,946,783 and 6,921,659, and Chen et al., *Biotechnology and Bioengineering* (2004) 85: 463-474, each of which is incorporated herein by reference.

In some embodiments, one or more genes described herein are expressed recombinantly in a bacterial cell. Bacterial cells described herein can be cultured in media of any type (rich or minimal) and any composition. In some embodiments, the cells are culture in minimal medium. As would be understood by one of ordinary skill in the art, routine optimization would allow for use of a variety of types of media. The selected medium can be supplemented with various additional components. Some non-limiting examples of supplemental components include glucose, antibiotics, isopropyl β-D-1-thiogalactopyranoside (IPTG), tetracycline or anhydro-tetracycline (aTc) for gene induction and ATCC Trace Mineral Supplement. Similarly, other aspects of the medium, and growth conditions of the cells of the embodiments described herein may be optimized through routine experimentation. pH and temperature are non-limiting examples of factors which can be optimized. In some embodiments, the concentration and amount of a supplemental component may be optimized. In some embodiments, how often the media is supplemented with one or more supplemental components, and the amount of time that the media is cultured is optimized.

Techniques for the manipulation of nucleic acids, e.g., subcloning, labeling probes (e.g., random-primer labeling using Klenow polymerase, nick translation, amplification), sequencing, hybridization, and the like are well described in the scientific and patent literature, see, e.g., Sambrook, Ed., *Molecular Cloning: A Laboratory Manual* (2nd Ed.) Vols 1-3, Cold Spring Harbor Laboratory (1989); Ausubel, Ed., *Current Protocols in Molecular Biology*, John Wiley & Sons, Inc., New York (1997); and Tijssen, Ed., *Laboratory Techniques in Biochemistry and Molecular Biology: Hybridization with Nucleic Acid Probes, Part I. Theory and Nucleic Acid Preparation*, Elsevier, N.Y. (1993), each of which is incorporated herein by reference.

It should be appreciated that the genes encoding targeted enzymes and site-specific proteases associated with the embodiments described herein can be obtained from a variety of sources. As one of ordinary skill in the art would be aware, homologous genes for these targeted enzymes and site-specific proteases exist in many species and can be identified by homology searches, for example through a protein BLAST search, available at the NCBI internet site (ncbi.nlm.nih.gov). Genes encoding these targeted enzymes and site-specific proteases can be PCR-amplified from DNA from any source which contains the given targeted enzyme and site-specific protease, for example using degenerate primers, as would be understood by one of ordinary skill in the art. In some embodiments, the gene encoding a given targeted enzyme and site-specific protease can be synthetic (artificial), for example, DNA synthesized from sugars, nitrogen-based compounds, phosphates, and other compound/reagents required for DNA synthesis. Any means of obtaining the genes encoding for the targeted enzymes and site-specific proteases discussed here are compatible with aspects of the embodiments described herein.

The embodiments described herein also provide isolated polypeptides and proteins (e.g., targeted enzymes and site-specific proteases) encoded by the nucleic acids. Such polypeptides are useful, for example, alone or as fusion proteins. Polypeptides associated with the cells, cell lysates, and methods described herein can be isolated from biological samples including tissue or cell homogenates, and can also be expressed recombinantly in a variety of prokaryotic and eukaryotic expression systems by constructing an expression vector appropriate to the expression system, introducing the expression vector into the expression system, and isolating the recombinantly expressed polypeptide or protein, e.g., a targeted enzyme or site-specific protease. Polypeptides can also be synthesized chemically using well-established methods of peptide synthesis. In some embodiments, isolated enzymes and/or protease may be added directly to cell lysates during the production phase of metabolite production.

A variety of methodologies well known to the skilled practitioner can be utilized to obtain isolated polypeptides associated with the embodiments described herein. The polypeptide may be purified from cells by chromatographic means or immunological recognition. Alternatively, an expression vector may be introduced into cells to cause production of the polypeptide. In another method, mRNA transcripts may be microinjected or otherwise introduced into cells to cause production of the encoded polypeptide. Translation of mRNA in cell free extracts such as the reticulocyte lysate system also may be used to produce polypeptides. Those skilled in the art also can readily follow known methods for isolating polypeptides. These include, but are not limited to, immunochromatography, HPLC, size exclusion chromatography, ion exchange chromatography and immune affinity chromatography.

The expression of the molecules, such as the targeted enzymes and site-specific proteases, described herein may be determined using routine methods known to those of ordinary skill in the art. These methods include, but are not limited to: direct RNA amplification, reverse transcription of RNA to cDNA, real-time RT-PCR, amplification of cDNA, hybridization, and immunologically based assay methods, which include, but are not limited to, immunohistochemistry, antibody sandwich capture assay, ELISA, and enzyme-linked immunospot assay (EliSpot assay). For example, the determination of the presence of level of nucleic acid molecules in a cell can be carried out via any standard nucleic acid determination assay, including the polymerase chain reaction (PCR), or assaying with labeled hybridization probes. Such hybridization methods include, but are not limited to microarray techniques.

The embodiments described herein thus involve, in one aspect, targeted enzymes and site specific proteases, genes encoding those enzymes and proteases, functional modifications and variants of the foregoing, as well as uses relating thereto.

The embodiments described herein also includes degenerate coding sequences which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating polypeptide. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the embodiments described herein embrace degenerate nucleic acids that differ from the biologically isolated nucleic acids in codon sequence due to the degeneracy of the genetic code. The embodiments also embraces codon optimization to suit optimal codon usage of a host cell, e.g., an E. coli or other bacterial cell.

The embodiments described herein also provides modified nucleic acid molecules which include additions, substitutions and deletions of one or more nucleotides. In some embodiments, these modified nucleic acid molecules and/or the polypeptides they encode retain at least one activity or function of the unmodified nucleic acid molecule and/or the polypeptides, such as enzymatic (e.g., protease) activity. In certain embodiments, the modified nucleic acid molecules encode modified polypeptides, for example, polypeptides having conservative amino acid substitutions as are described elsewhere herein. The modified nucleic acid molecules are structurally related to the unmodified nucleic acid molecules, and in some embodiments are sufficiently structurally related to the unmodified nucleic acid molecules so that the modified and unmodified nucleic acid molecules hybridize under stringent conditions known to one of skill in the art.

For example, modified nucleic acid molecules which encode polypeptides having single amino acid changes can be prepared. Each of these nucleic acid molecules can have one, two or three nucleotide substitutions exclusive of nucleotide changes corresponding to the degeneracy of the genetic code as described herein Likewise, modified nucleic acid molecules that encode polypeptides having two amino acid changes can be prepared which have, e.g., 2-6 nucleotide changes. Numerous modified nucleic acid molecules like these will be readily envisioned by one of skill in the art, including for example, substitutions of nucleotides in codons encoding amino acids 2 and 3, 2 and 4, 2 and 5, 2 and 6, and so on. In the foregoing example, each combination of two amino acids is included in the set of modified nucleic acid molecules, as well as all nucleotide substitutions which code for the amino acid substitutions. Additional nucleic acid molecules that encode polypeptides having additional substitutions (e.g., 3 or more), additions or deletions (e.g., by introduction of a stop codon or a splice site(s)) also can be prepared as readily envisioned by one of ordinary skill in the art. Any of the foregoing nucleic acids or polypeptides can be tested by routine experimentation for retention of structural relation or activity, e.g., enzymatic activity, to the nucleic acids and/or polypeptides disclosed herein.

In certain embodiments, variants of the targeted enzymes and site-specific proteases described herein are contemplated. As used herein, a "variant" of an targeted enzyme or site-specific protease is a protein which contains one or more modifications to the primary amino acid sequence of the targeted enzyme or site-specific protease. Modifications which create a variant can be made to an targeted enzyme or site-specific protease, for example, to reduce or eliminate an activity of the targeted enzyme in the presence of the site-specific protease or to alter the cellular distribution of the site-specific protease.

Modifications to a targeted enzyme or a site-specific protease may be made to the nucleic acid which encodes the protein, and can include deletions, point mutations, truncations, amino acid substitutions and additions of amino acids or non-amino acid moieties. Alternatively, modifications can be made directly to the polypeptide(s) or protein, such as by cleavage, addition of a linker molecule, addition of a detectable moiety, such as biotin, addition of a fatty acid, and the like. Modifications also embrace fusion proteins. One of skill in the art will know methods for predicting the effect on protein conformation of a change in amino acid sequence, and can thus "design" a variant targeted enzyme or site-specific protease according to those known methods. One example of such a method is described by Dahiyat and Mayo in *Science* 278:82 87, 1997, whereby proteins can be designed de novo. The method can be applied to a known protein to vary only a portion of the protein sequence. By applying the computational methods of Dahiyat and Mayo, specific variants of a protein can be proposed and tested to determine whether the variant retains a desired conformation.

In some embodiments, variants include targeted enzymes and site-specific proteases that are modified specifically to alter a feature of the protein unrelated to its desired physiological activity. For example, cysteine residues can be substituted or deleted to prevent unwanted disulfide linkages. Similarly, certain amino acids can be changed to enhance expression of a protein by eliminating proteolysis by proteases in an expression system (e.g., dibasic amino acid residues in yeast expression systems in which KEX2 protease activity is present).

Mutations of a nucleic acid which encode a targeted enzyme or site-specific protease may preserve the amino acid reading frame of the coding sequence, and in some instances, do not create regions in the nucleic acid which are likely to hybridize to form secondary structures, such a hairpins or loops, which can be deleterious to expression of the variant protein.

Mutations can be made by selecting an amino acid substitution, or by random mutagenesis of a selected site in a nucleic acid which encodes the targeted enzyme or site-specific protease. Variant proteins are then expressed and tested for one or more activities to determine which mutation provides a variant enzyme or protease with the desired properties, e.g., site-specific protease cleavage. Further mutations can be made to variants (or to non-variant proteins) which are silent as to the amino acid sequence of the protein, but which provide codons for efficient translation in a particular host. Examples of codons for efficient translation of a nucleic acid in, e.g., *E. coli*, are well known to those of ordinary skill in the art. Still, other mutations can be made to the noncoding sequences of a gene or cDNA clone to enhance expression of the protein. The activity of variants of protein can be tested by cloning the gene encoding the variant protein into a bacterial or mammalian expression vector, introducing the vector into an appropriate host cell, expressing the variant protein, and testing for a functional capability of the protein as disclosed herein.

The skilled artisan will also know that conservative amino acid substitutions may be made in proteins to provide functionally equivalent variants of the foregoing targeted enzymes and site-specific proteases, i.e., the variants retain the functional capabilities of the proteins. As used herein, a "conservative amino acid substitution" refers to an amino acid substitution which does not alter the relative charge or size characteristics of the protein in which the amino acid substitution is made. Variants can be prepared according to methods for protein sequence known to one of ordinary skill in the art such as are found in references which compile such methods, e.g., *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary functionally equivalent variants of the protein include conservative amino acid substitutions in the amino acid sequences of the enzymes and proteases disclosed herein. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

In certain embodiments, fewer than all of the amino acids can be changed when preparing variant enzymes and proteases. Where particular amino acid residues are known to confer function and function is required, such amino acids will not be replaced, or alternatively, will be replaced by conservative amino acid substitutions. In some embodiments, 1, 2, 3, 4, 5, 6, 7, 8, 9, 10, 11, 12, 13, 14, 15, 16, 17, 18, 19, 20 residues are changed when preparing variant proteins. It some embodiments, the fewest number of substitutions is made. Thus, one method for generating variant enzymes or proteases is to substitute all other amino acids for a particular single amino acid, then determine the activity of the variant, then repeat the process with one or more of the enzymes or proteins having the best activity.

Conservative amino-acid substitutions in the amino acid sequence of protein to produce functionally equivalent variants of protein may be made by alteration of a nucleic acid encoding a targeted enzyme or site-specific protease. Such substitutions can be made by a variety of methods known to one of ordinary skill in the art. For example, amino acid substitutions may be made by PCR-directed mutation, site-directed mutagenesis according to the method of Kunkel (Kunkel, Proc. Nat. Acad. Sci. U.S.A. (1985) 82: 488-492), or by chemical synthesis of a gene encoding a protein. For example, in some embodiments, a nucleic acid encoding a targeted enzyme is modified to comprises a site-specific protease cleavage site, and the expressed enzyme variant still retains the functional activity of the unmodified enzyme.

Vectors and Expression Constructs

Vectors useful for the transformation of an isolated DNA fragment encoding a targeted enzyme and/or a site-specific protease into suitable host cells (e.g., *E. coli* cells) are well known in the art. As used herein, a "vector" may be any of a number of nucleic acids into which a desired sequence or sequences (e.g., sequences encoding targeted enzymes or site-specific proteases) may be inserted by restriction and ligation for transport between different genetic environments or for expression in a host cell. Vectors are typically composed of DNA, although RNA vectors are also available. Vectors include, but are not limited to, plasmids, fosmids, phagemids, virus genomes, and artificial chromosomes. The vector can contain sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment that controls transcriptional termination. Vectors may also be used which promote the integration of the chimeric gene encoding a fusion protein into the host cell genome. Such vectors may be for random integration, site-directed integration, or for homologous recombination. A vector may have features allowing single cross-over or double-crossover types of homologous recombination. One or multiple copies may be integrated into a host cell (e.g., bacterial or yeast cell) genome.

A cloning vector is able to replicate autonomously or integrated in the genome in a host cell. A cloning vector is further characterized by one or more endonuclease restriction sites at which the vector may be cut (e.g., via enzymatic digestion) in a determinable fashion and into which a desired DNA sequence may be ligated. In this way, the new recombinant vector retains its ability to replicate in the host cell. When plasmid vectors are used, replication of the desired sequence may occur many times as the plasmid increases in copy number within the host or just a single time per host before the host reproduces by mitosis. When phage vectors are used, replication may occur actively during a lytic phase or passively during a lysogenic phase.

An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase, or alkaline phosphatase), and genes which visibly affect the phenotype of transformed or transfected cells, hosts, colonies or plaques (e.g., green fluorescent protein). Vectors include those capable of autonomous replication and expression of the structural gene products present in the DNA segments to which they are operably joined.

As used herein, a coding sequence and regulatory sequences are said to be "operably" linked or joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frameshift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript can be translated, for example, into the desired site-specific protease.

When the nucleic acid molecule that encodes any of the targeted enzymes or site-specific proteases described herein is expressed in a cell, a variety of transcription control sequences (e.g., promoter/enhancer sequences) can be used to direct its expression. The promoter can be a native promoter, i.e., the promoter of the gene in its endogenous context, which provides normal regulation of expression of the gene. In some embodiments the promoter can be constitutive, i.e., the promoter is unregulated allowing for continual transcription of its associated gene. A variety of conditional promoters also can be used, such as promoters controlled by the presence or absence of a molecule. For example, some inducible promoters are activated by chemicals such as isopropyl β-D-1-thiogalactopyranoside (IPTG) or Tetracycline (Tet).

The precise nature of the regulatory sequences needed for gene expression may vary between species or cell types, and may include, as necessary, 5' non-transcribed and 5' non-translated sequences involved with the initiation of transcription and translation respectively, such as a TATA box, capping sequence, CAAT sequence, and the like. In particular, such 5' non-transcribed regulatory sequences will include a promoter region which includes a promoter sequence for transcriptional control of the operably joined gene. Regulatory sequences may also include enhancer sequences or upstream activator sequences as desired. Vectors may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by introducing into the cells heterologous DNA (or RNA). That heterologous DNA (or RNA) is placed under operable control of transcriptional elements to permit the expression of the heterologous DNA in the host cell. In some embodiments two or more nucleic acids may be cloned into the same expression vector or plasmid.

The methods described herein may make use of constitutive or regulated expression of various nucleic sequences encoding the targeted enzymes and/or site-specific proteases. Expression may be regulated by various cues, for example, induction by chemicals (e.g., IPTG), change of growth phase, depletion of a nutrient, temperature shifts (e.g., heat shock promoter), and/or light. In some embodiments, inducible promoters are regulated by the presence of an inducing agent, for example, a chemical such as lactose, arabinose, or tetracycline, as known in the art. Where "high level" expression is indicated, the concentration of the expressed protein in the cell can be at least about 2-fold above basal levels, at least 10-fold above basal levels, at least 25-fold above basal levels, at least 50-fold above basal levels, or more, e.g., between about 2-fold to about 100-fold above basal levels.

It may be desirable to experimentally adjust expression rate to optimize efficiency of cell or cell compartment export of the site-specific proteases described herein. Poor translocation, for example, to the periplasm of a cell can result from insufficient capacity of export machinery. Methods for adjustment of expression rate of the site-specific protease include, without limitation, modification of copy number of the plasmid carrying the gene coding for the protease to be exported to the periplasm. Replicons known and used in the art include P15A (10 copies/cell), ColA (30 copies/cell), ColE1 (40 copies/cell), and RSF1030 (>100 copies/cell). The ribosome binding site in the 5' UTR of the gene coding for the protease to be exported to the periplasm may be modified, where a library of ribosome binding sites with varying strengths can be created and tested; see, e.g., Salis et al., *Nature Biotechnology* (2009) 27: 946-950; and Simmons et al., *Nature Biotechnology* (1996) 14:629-634, each incorporated herein by reference. The promoter region upstream of the gene coding for the protease to be exported may be modified to adjust the rate of transcription, where a library of promoter regions with varying strengths can be created and tested; see, e.g., Alper et al., PNAS (2005) 102:12678-12683; and De Mey et al., *BMC Biotechnology* (2007) 7:34, each of which is incorporated herein by reference.

Inducible Expression

The methods described herein may make use of regulated expression of various coding sequences. Expression may be regulated by various cues, for example, induction by chemicals, change of growth phase, depletion of a nutrient, temperature shifts, and light. In some embodiments inducible promoters regulated by the presence of an inducing agent, e.g. a chemical such as lactose, arabinose, and tetracycline, known in the art.

Expression and cloning vectors usually contain a promoter that is recognized by the host organism and is operably linked to the coding sequence of interest. Promoters are untranslated sequences located upstream (5') to the start codon of a structural gene that control the transcription and translation of particular nucleic acid sequence to which they are operably linked. Such promoters may fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known. While the native promoter may be used, in some embodiments, heterologous promoters are used, as they may permit greater transcription of the targeted enzyme or site-specific protease and higher yields.

Promoters suitable for use with prokaryotic hosts include the β-lactamase and lactose promoter systems, alkaline phosphatase, a tryptophan (trp) promoter system, and numerous hybrid promoters such as the tac promoter. However, other known bacterial promoters are also suitable, e.g., the lacI promoter, the T3 promoter, the T7 promoter, the arabinose promoter, the gpt promoter, the lambda PR promoter, the lambda PL promoter, promoters from operons encoding glycolytic enzymes such as 3-phosphoglycerate kinase (PGK), and the acid phosphatase promoter. Their nucleotide sequences have been published, thereby enabling a skilled worker to operably ligate them to a sequence of interest using linkers or adapters. Promoters for use in bacterial systems also will contain a Shine-Dalgarno (S.D.) sequence operably linked to the coding sequence. In certain cases, also, the host cell may be modified genetically to adjust concentrations of metabolite or inducer transporter proteins so that all cells in a culture will be induced equivalently.

Promoters suitable for eukaryotic cells, e.g. yeast cells, are also known in the art. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly-A tail to the 3' end of the coding sequence. All of these sequences are suitably inserted into eukaryotic expression vectors. Examples of suitable promoting sequences for use with yeast hosts include the promoters for 3-phosphoglyceratekinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Yeast enhancers also are advantageously used with yeast promoters.

EXAMPLES

The following examples are put forth so as to provide those of ordinary skill in the art with a complete disclosure and description of how to make and use the embodiments described herein, and are not intended to limit the scope of the invention or to represent that the experiments below are all or the only experiments performed. Efforts have been made to ensure accuracy with respect to numbers used (e.g., amounts, temperature, and the like), but some experimental errors and deviations may be present. Unless indicated otherwise, parts are parts by weight, molecular weight is average molecular weight, temperature is in degrees Celsius, and pressure is at or near atmospheric pressure.

Segregating site-specific protease. The steps in the process of protease segregation and target enzyme engineering include (i) analyzing a pathway to identify an enzyme or enzymes to be targeted for inactivation, (ii) engineering a protease cleavage site by modifying the DNA sequence that encodes the targeted enzyme(s), (iii) verifying activity of the targeted enzyme, (iv) engineering periplasmically segregated proteases, (v) verifying activity of periplasmically-expressed proteases, (vi) demonstrating metabolically healthy cell growth, and (vii) demonstrating target enzyme(s) inactivation and increased flux to the product of interest post-lysis in an active, cell-free reaction.

Example 1

Protease Segregation to Periplasm

A library of plasmids is constructed containing several protease genes with various periplasmic signal sequences targeting the protease enzymes to the periplasm. For example, five specific proteases and six periplasmic signal sequences could be combined to make a library of thirty members.

Nucleotide sequences coding for periplasmic signal sequences are added to each protease gene through polymerase chain reaction (PCR) amplification. Alternatively, the protease genes are synthesized to contain the periplasmic leader signal sequence. Complete synthesis enables codon optimization for efficient expression in the host strain. Suitable proteases and periplasmic targeting/leader sequences are described above in Tables 2 and 3, respectively.

The library of periplasmically-targeted protease genes is subcloned into a pDuet vector, or other suitable vector, for inducible expression. E. coli strain BL21(DE3), or similar strain expressing the T7 polymerase, is transformed with the periplasmically-targeted protease library. Expression modification is achieved through use of varying levels of isopropyl β-D-1-thiogalactopyranoside (IPTG) (each vector expresses LacI, and the T7 promoter contains a lac operator site), through use of various promoters and ribosome binding sites, as well as through use of copy number variation among different pDuet vectors. Other plasmids, expression systems, or strains familiar to those skilled in the art may also be used.

Separate cultures harboring individual library members are grown to intermediate optical density (OD) in rich defined media prior to expression induction with 0.02-1 mM IPTG. Expression is induced for several hours to enable buildup of protease in the periplasm. Post-induction growth is monitored to determine which library members, if any, hinder cell growth presumably due to off-target cleavage of native E. coli periplasmic proteins. Severe growth inhibition may indicate that the expressed, active protease targets an important or essential protein(s). This may be alleviated by identifying the off-target protein(s) and modifying their amino acid sequence(s) to eliminate the specific cleavage site(s). Periplasmically-targeted protease is extracted using osmotic shock, or other methods known to those skilled in the art. Verification of expression of full-length protein is determined by denaturing protein gel electrophoresis with appropriate size standards. More efficient periplasmic export can be achieved by optimizing expression through use of varying IPTG levels, differing plasmid origins of replication on the plasmid being used, and/or modification of ribosomal binding site (RBS).

The specific activity of periplasmically-targeted protease is determined in periplasmic extract by designing a target protein that contains a cleavage site and that, upon cleavage by the site-specific protease, will give a measurable signal. One example is outlined by Sarath and Schwartzbach in *Current Protocols in Protein Science* (2001) 21.9.1-21.9.10. This method includes the use of a fluorescent reporter protein containing a purification tag on either the N- or C-terminus. A cleavage site is inserted between the purification tag and the open reading frame of the fluorescent reporter, creating a target for a specific protease. Purified reporter target can be added to periplasmic extract containing the site-specific protease, and this mixture can be separated using an affinity resin that binds the purification tag. Cleaved, unbound fluorescent reporter is separated, and fluorescence is measured to determine the extent of protease cleavage. Alternatively, the engineered fluorescent reporter can be expressed in the cytoplasm of the strain expressing a periplasmically-targeted protease. Uncleaved reporter can be separated from the lysate, and the level of fluorescence in the lysate can be used to determine the extent of protease target cleavage.

A specific non-limiting example of a pathway is the pathway for the synthesis of shikimic acid. In this pathway, for example, a reaction between the cellular commodity compounds phosphoenolpyruvate ($S_{1A}$) and erythrose-4-phosphate ($S_{1B}$) is catalyzed by the isoenzymes of DAHP synthase, AroF, G, or H ($E_1$) to form 3-deoxy-D-arabinoseheptulose-7-phosphate (DAHP). DAHP ($S_2$) is transformed to 3-dehydroquinate (3-DHQ) by the second enzyme in the pathway, DHQ synthase, AroB ($E_2$). 3-DHQ ($S_3$) is dehydrated to 3-dehydroshikimate by the third enzyme in the pathway, 3-DHQ dehydratase, AroD ($E_3$). 3-dehydroshikimate ($S_4$) is reduced to shikimic acid ($P_F$) by the fourth enzyme in the pathway, shikimate dehydrogenase, AroE ($E_4$), using NADPH as a cofactor. The enzymes of the pathway are known in the art and have been characterized in a number of organisms, including, for example, *E. coli*, in which the enzymes are encoded by the genetic loci as follows: DAHP synthase (aroG, F, or H); DHQ synthase (aroB); 3-DHQ dehydratase (aroD); shikimate dehydrogenase (aroE).

In the shikimic acid pathway, the overexpression of aroE, aroF, and tktA has been shown to increase the production of shikimic acid either directly with aroE and aroF, or indirectly with tktA, which increases the supply of the substrate molecule erythrose-4-phosphate.

There are also competing enzymes relevant to this pathway, which utilize the desired final product as a substrate, which enzymes are shikimate kinase (AroK) and shikimate kinase II (AroL). The presence of active competing enzymes may be undesirable, as they reduce the amount of desired product in the reaction mixture.

The sequence encoding the competing enzyme, shikimate kinase II (Genbank accession number NP_414922.1) is made susceptible to proteolysis by a site-specific protease, by introducing a protease cleavage site in the target protein through introduction of specific mutations, by recombination, or multiplex genome engineering. The site for protease inactivation is introduced at a suitable site in the enzyme. Alternatively, shikimate kinase II is inactivated by the methods set forth in Datsenko and Wanner (2000), and shikimate kinase I is made susceptible to proteolysis by a site-specific protease.

Included in the production of shikimic acid may be expression of DAHP synthase and/or additional enzymes in the biochemical pathway to shikimic acid:

TABLE 4

Examples of enzymes in the shikimic acid biochemical pathway.

| EC# | Enzyme | Gene |
|---|---|---|
| 2.2.1.1 | transketolase | tktA |
| 4.2.3.4 | dehydroquinate synthase | aroB |
| 4.2.1.10 | dehydroquinate dehydratase | aroD |
| 1.1.1.25 | shikimate dehydrogenase | aroE |

The sequence of the enzyme is analyzed to identify the amino acid sequence closest to the protease cleavage motif, so that the least number of modifications to the amino acid sequence is needed to result in a protease cleavage site. The ideal site is on the surface of the protein, to minimize the effects on enzyme function. A site near the surface also ensures that it is accessible to the protease when folded. Alternatively, an enzyme from a different organism that carries out the same function and contains a protease cleavage site can be used instead of a native enzyme that is not protease labile.

A suitable site for cleavage (a slash indicates alternative amino acids) is the sequence ENLYFQ$^{G/S}$ (SEQ ID NO:20) (cleaved by the tobacco etch virus protease). An alternative site for cleavage is GARR$^{G/S}$ (SEQ ID NO:21) (cleaved by the yellow fever virus protease). An alternative site for cleavage is LVPRGS (SEQ ID NO:22) (cleaved by thrombin). An alternative site for cleavage is I$^{E/D}$GR (SEQ ID NO:23) (cleaved by thrombin). The genetically modified sequence, which may be referred to the protease-labile form of the sequence, is expressed from a plasmid with concomitant inactivation of the chromosomal copy, or used to alter the chromosomal sequence of the host organism. In an alternative embodiment, the gene that encodes AroL is inactivated, and AroK is made susceptible to proteolysis.

Enzymatic assays are conducted, after a brief scanning of the sequences, to ensure that the chosen protease cleaves the target protein but not any other protein needed for shikimic acid biosynthesis. To accomplish this, the cells modified with the protease-labile competing enzyme are further modified to express the cognate protease under the control of an inducible promoter. The cells are grown in medium containing glucose as a carbon source. The production of shikimic acid in the cells is measured using nuclear magnetic resonance ($^1$HNMR) spectroscopy or high-performance liquid chromatography (HPLC), as described by Knop et al. (2001) *J. Am. Chem. Soc.* 123:10173-10182 or van Hess et al. (1999) *Talanta*, 5 Jan. 1999, Pages 173-17], or any other analytical chemistry technique, such as GC-MS.

Alternatively individual enzymatic assays, e.g., in which the depletion of an enzymatic substrate or accumulation of its product is measured in a solution with the purified enzyme protein, are performed.

If any protein in the shikimic acid pathway is found to be susceptible to proteolysis, other than the competing enzyme(s), cleavage sites are removed by making conservative amino acid changes by site-directed mutagenesis. Alternatively, an enzyme from a different organism that carries out the same function, but does not contain a protease cleavage site, can be used instead of a native enzyme that is protease labile. Such analysis is repeated if needed until an appropriate protease is found.

Example 2

Expression and Activity of Periplasmically-Targeted Enterokinase

Plasmids, cell growth and expression. The gene coding for bovine enterokinase (Genbank Accession L19663.1) was chemically synthesized with codon content optimized for expression in *E. coli* and with the following periplasmic signal sequences:

TABLE 5

Periplasmic signal sequences

| | |
|---|---|
| DsbA (DA) | atgaaaaagatttggctggcgctggctg-gtttagttttagcgttta gcgcatcggcg (SEQ ID NO: 17) |
| OmpA (OA) | atgaaaaaaacggcaattgcgatagcg-gttgcgctagctggttttg ccacggtggcgcaggct (SEQ ID NO: 18) |
| MalE (ME) | atgaaaataaaaacaggtgcacgcatc-ctcgcattatccgcattaa cgacgatgatgttttccgcctcggctctcgcc (SEQ ID NO:19) |

These constructs were subcloned into pACYC-Duet (EMD Chemicals, Gibbstown, N.J.), and *E. coli* strain BL21(DE3) was transformed with the resulting plasmids. 250 ml cultures were grown from glycerol stocks for 6 h at 37° C. and 300 rpm in EZ rich medium with 34 µg/ml chloramphenicol (cam) to an optical density (OD600) of 0.6-0.8. A strain carrying the empty pACYC-Duet vector was used as a control. Expression was induced with 0.1 mM isopropyl β-D-1-thiogalactopyranoside (IPTG), and cultures were grown for 16 h at 25° C. After induction, cells were harvested and the periplasmic fraction was extracted.

Periplasmic extraction and activity assay. Cells were harvested from 12 ml of culture by centrifugation at 3000×g for 30 min at 4° C. The supernatant was discarded, and the cell pellet was gently re-suspended in 2 ml ice-cold 1 mM Tris-HCl. This suspension was then centrifuged at 3000×g for 30 min at 4° C. The supernatant was collected as the periplasmic fraction. Activity assays were conducted by incubating 3.6 µg of the periplasmic fraction with 4 µg of control protein (an enterokinase cleavable protein provided by EMD) in reaction buffer containing 50 mM NaCl, 20 mM Tris-HCl, 2 mM CaCl$_2$ pH 7.4. The reactions were incubated at 30° C. for 24 h. The reactions were quenched by adding 19.5 µL of sodium dodecyl sulfate (SDS)-PAGE running buffer containing 0.04 M dithiothreitol (DTT), and boiling at 99° C. for 5 min. Reactions were run on a NuPAGE® 12% Bis-Tris Gel at 200 V for 50 minutes, and gels were stained with Coomassie dye. Cleavage of the 48 kDa control protein by enterokinase (EK) gives two proteolytic fragments of 32 and 16 kDa. The gels shown in FIG. 1 were used to visualized the protease cleavage products and indicate that the periplasmically localized enterokinase is active in cleaving the target protein.

Example 3

Expression of Periplasmically-Targeted Enterokinase

The gene sequence for bovine enterokinase was codon-optimized for expression in *E. coli* and subcloned into the expression vector pACYCDuet-1 (Novagen) with the addition of the OmpA periplasmic expression signal sequence. The construct was transformed into *E. coli* strain BL21(DE3). Cells were grown to an optical density (OD600) of 0.6, expression was induced by addition of 0.8 mM IPTG and continued growth at 37° C. for 3 hours. The culture underwent 2.4 doublings during induction, indicating that enterokinase expression did not inhibit growth. Cells were harvested by centrifugation, resuspended in assay buffer (20 mM Tris HCl pH 7.4; 50 mM NaCl; 2 mM CaCl$_2$) and lysed using a homogenizer.

Example 4

Enterokinase Activity in Whole-Cell Lysate

Figure 2:
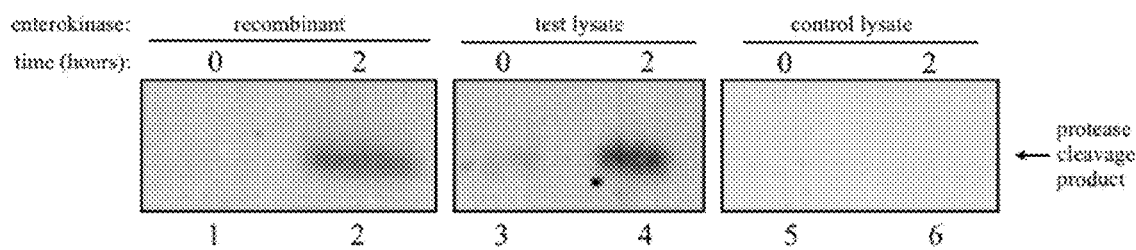
FIG. 2 depicts images of an immunoblot of samples taken after cleavage incubations using cell extracts obtained from control cultures, from periplasmically-targeted site-specific enterokinase cultures, as well as from purified recombinant enterokinase.

Whole cell lysate from enterokinase-expressing cells was tested for protease activity by incubation with a cleavage control protein containing an enterokinase cleavage site (Asp-Asp-Asp-Asp-Lys) (SEQ ID NO:26) and compared to the activity of recombinant enterokinase. Recombinant enterokinase and cleavage control protein were obtained from Novagen. 40 µl of lysate or 2 units of recombinant enterokinase in 40 µl of assay buffer (20 mM Tris HCl pH 7.4; 50 mM NaCl; 2 mM CaC12) were incubated with 4 µg of cleavage control protein at room temperature. A similarly prepared lysate from a strain not expressing enterokinase was used as a negative control. Zero- and 2-hour samples were analyzed by immunoblot with S protein horseradish peroxidase (HRP) conjugate that recognizes the amino terminal S tag on the cleavage control protein. FIG. 2 shows detection of the 16 kDa protease cleavage fragment. The target protein was specifically cleaved by recombinant enterokinase (lane 2) and by lysate from a strain expressing periplasmically-targeted enterokinase (lane 4), but not by a lysate lacking enterokinase expression (lane 6).

Example 5

Target Enzyme Inactivation by Protease Release from the Periplasm

The gene sequence for bovine enterokinase is codon optimized for expression in *E. coli* cells and subcloned into an inducible plasmid expression vector with the addition of a periplasmic expression signal sequence. A gene that encodes the AroL enzyme is modified to include a enterokinase-specific cleavage site. *E. coli* cells are modified to express the site-specific protease in the periplasm and the modified target enzyme in the cytoplasm. The cells are grown to an optical density (OD600) of 0.6, expression of the enterokinase is induced, and the cells are allowed to continue to growth at 37° C. for 3 hours.

Cells are lysed using a homogenizer, thereby bringing into contact the site-specific protease and the modified enzyme. The cell lysate is combined with one or more substrates, enzymes, nutrients, co-factors, buffers, reducing agents, and/or ATP generating systems, as required for activity of the pathway enzymes, thereby forming a cell-free system. The redox potential, pH, and ionic strength of the cell-free system is optimized. The production of shikimic acid in the cell-free system is measured using $^1$HNMR spectroscopy or HPLC.

Example 6

PurF Inactivation by Protease Release from the Periplasm

A library is generated, each member of which encodes an amidophosphoribosyl transferase enzyme (*E. coli* PurF) that contains an enterokinase-specific cleavage site at different locations within the polypeptide sequence of the enzyme. Choice of cleavage site location is aided by the published PurF tertiary structure as reported in Muchmore et al., *Protein Science* (1998) 7:39-51. For example, Muchmore et al.

describes a region comprising a flexible solvent exposed loop that is suitable for cleavage site incorporation. The library is generated by PCR, gene synthesis or other standard molecular biology methods and constructed in vectors for controlled expression in *E. coli* cells. *E. coli* cells are transformed with the vectors expressing the modified enzyme library. The cells are grown to an optical density (OD600) of 0.6, expression of the library is induced, and the cells are allowed to continue growth at 37° C. for 3 hours.

Cells are lysed using a homogenizer, and cell lysate is treated with purified recombinant enterokinase (Novagen) to verify enterokinase-mediate cleavage of library members. Cleavage of PurF is monitored by SDS-PAGE. Library members that are cleaved by recombinant enterokinase are then tested for activity. Specifically, lysate from cells overexpressing these library members is combined with PRPP and glutamine (10 mM each), as required for enzyme activity, thereby forming a cell-free system. Samples of the reaction are analyzed at a series of time points. The activity of modified PurF is monitored by the appearance of glutamate and the concomitant disappearance of glutamine in the cell-free reaction as measured by HPLC using pre-column derivatization with orthophthalaldehyde. Inactivation of modified PurF is tested by addition of recombinant enterokinase to the assay described above.

The most active members of the PurF library that show activity in the absence of enterokinase, and are cleaved and inactivated by enterokinase in the course of the reaction, are chosen for integration into a cell containing a pathway of interest that is inhibited by PurF activity (e.g., a pathway requiring PRPP, such as a pathway producing a pyrimidine-derived compound). The cell additionally contains periplasmically expressed enterokinase and any enzymes required for the pathway of interest. The library member is knocked into the chromosomal locus of PurF, thus replacing the endogenous gene. It is verified that growth is not adversely affected by gene replacement.

Cells are lysed using a homogenizer, thereby bringing into contact the site-specific protease and the modified enzyme. The cell lysate is combined with one or more substrates, enzymes, nutrients, co-factors, buffers, reducing agents, and/or ATP generating systems, as required for activity of the pathway enzymes, thereby forming a cell-free system. The redox potential, pH, and ionic strength of the cell-free system is optimized. The production of the product of interest in the cell-free system is measured using appropriate methods.

Other Embodiments

Unless defined otherwise, all technical and scientific terms used herein have the same meaning as is commonly understood by one of ordinary skill in the art. All patents, patent applications (published or unpublished), and other publications referred to herein are incorporated by reference in their entireties. If a definition set forth in this application is contrary to or otherwise inconsistent with a definition set forth in the patents, applications, published applications and other publications that are incorporated herein by reference, the definition set forth in this application prevails over the definition that is incorporated herein by reference.

Citation of publications or documents is not intended as an admission that any of such publications or documents are pertinent prior art, nor does it constitute any admission as to the contents or date of these publications or documents.

As used herein, "a" or "an" means "at least one" or "one or more" unless otherwise indicated.

As used herein, the term "about" and "approximately" are used interchangeably, and the meaning of the terms can be obtained by considering the context of the terms as they are used in the specification and claims of the application. In some embodiments, "about" a particular numerical value encompasses a range of 30% of the value. In other embodiments, "about" a particular numerical value encompasses a range of 20% of the value. In yet other embodiments, "about" a particular numerical value encompasses a range of 10% of the value.

---

What is claimed is:

1. A method of producing a product of a biosynthetic pathway of interest, the method comprising:
   (i) growing genetically modified bacterial cells that comprise nucleic acids that encode:
      (a) enzymes of the biosynthetic pathway of interest that catalyze production of the product,
      (b) a targeted enzyme that competes for substrates or cofactors with an enzyme in the biosynthetic pathway of interest, decreases the overall yield and/or the rate of production of the product, and includes a site-specific protease recognition sequence, and
      (c) a site-specific protease that cleaves the site-specific protease recognition sequence of the targeted enzyme and is genetically modified to include a periplasmic targeting sequence;
   (ii) lysing at least a portion of the bacterial cells to produce a lysate, thereby bringing the site-specific protease into contact with the targeted enzyme to cleave and inactivate or reduce the activity of the targeted enzyme;
   (iii) adding substrate to the lysate; and
   (iv) incubating the lysate and substrate, thereby producing the product of the biosynthetic pathway of interest.

2. The method of claim 1, wherein the method further comprises combining the cell lysate with one or more substrates, enzymes, nutrients, co-factors, buffers, reducing agents, or ATP generating systems.

3. The method of claim 1, wherein the periplasmic targeting sequence is selected from the group consisting of:

| | |
|---|---|
| MKIKTGARILALSALTTMMFSASALA, | (SEQ ID NO: 1) |
| MKKTAIAIAVALAGFATVAQA | (SEQ ID NO: 2) |
| MKQSTIALALLPLLFTPVTKA, | (SEQ ID NO: 3) |
| MMITLRKLPLAVAVAAGVMSAQAMA, | (SEQ ID NO: 4) |
| MNKKVLTLSAVMASMLFGAAAHA, | (SEQ ID NO: 5) |
| MKYLLPTAAAGLLLLAAQPAMA, | (SEQ ID NO: 6) |
| MKKNIAFLLASMFVFSIATNAYA | (SEQ ID NO: 7) |
| MKKIWLALAGLVLAFSASA, | (SEQ ID NO: 8) |
| MMTKIKLLMLIIFYLIISASAHA, | (SEQ ID NO: 9) |
| MKQALRVAFGFLILWASVLHA, and | (SEQ ID NO: 10) |
| MRVLLFLLLSLFMLPAFS. | (SEQ ID NO: 11) |

4. The method of claim 1, wherein the site-specific protease is selected from the group consisting of: TEV NIa, HRV 3C, enterokinase, Factor Xa, and thrombin.

5. The method of claim 1, wherein the targeted enzyme is genetically modified to include the site-specific protease recognition sequence.

6. The method of claim 1, wherein the nucleic acid encoding the site-specific protease is operably linked to an inducible promoter.

7. The method of claim 1, wherein the enzyme in the biosynthetic pathway of interest that competes with the targeted enzyme increases the rate of precursor supplied to the biosynthetic pathway of interest.

8. The method of claim 7, wherein the enzyme in the biosynthetic pathway of interest that competes with the targeted enzyme is a key pathway entry enzyme of the biosynthetic pathway of interest.

9. The method of claim 1, wherein the enzyme in the biosynthetic pathway of interest that competes with the targeted enzyme supplies a substrate or cofactor of the biosynthetic pathway of interest.

10. The method of claim 1, wherein a gene encoding the native counterpart of the targeted enzyme is replaced with a gene coding for the targeted enzyme.

11. The method of claim 1, wherein the gene encoding the native counterpart enzyme is knocked out.

12. The method of claim 1, wherein the targeted enzyme is over-expressed in the bacterial cell.

13. The method of claim 1, wherein the targeted enzyme is present on either an episomal vector or a chromosome.

14. The method of claim 1, wherein the product is shikimic acid, shikimate, poly-3-hydroxybutyrate, isobutanol, or 1-butanol.

15. The method of claim 1, wherein the activity of the targeted enzyme is reduced by about 50% upon cleavage by the protease.

16. The method of claim 15, wherein the activity of the targeted enzyme is reduced by about 90% upon cleavage by the protease.

17. The method of claim 1, wherein the targeted enzyme is essential for growth of the bacterial cell.

18. The method of claim 1, wherein the bacterial cell is an *Escherichia coli* cell.

19. The method of claim 1, wherein the product is a polymer.

20. The method of claim 1, wherein the product is selected from the group consisting of antibiotics, biosurfactants, biological fuels, amino acids, organic acids, fatty acids, alcohols, polyols, flavors, fragrances, nucleotides, vitamins, pigments, sugars, polysaccharides, plastics, isoprenoids, and terpenes.

21. The method of claim 15, wherein the activity of the targeted enzyme is reduced by about 60% upon cleavage by the protease.

22. The method of claim 15, wherein the activity of the targeted enzyme is reduced by about 70% upon cleavage by the protease.

23. The method of claim 15, wherein the activity of the targeted enzyme is reduced by about 80% upon cleavage by the protease.

24. The method of claim 15, wherein the activity of the targeted enzyme is reduced by about 90% upon cleavage by the protease.

* * * * *

SEQUENCE LISTING

```
<160> NUMBER OF SEQ ID NOS: 26

<210> SEQ ID NO 1
<211> LENGTH: 26
<212> TYPE: PRT
<213> ORGANISM: E. coli

<400> SEQUENCE: 1

Met Lys Ile Lys Thr Gly Ala Arg Ile Leu Ala Leu Ser Ala Leu Thr
1               5                   10                  15

Thr Met Met Phe Ser Ala Ser Ala Leu Ala
            20                  25

<210> SEQ ID NO 2
<211> LENGTH: 21
<212> TYPE: PRT
<213> ORGANISM: E. coli

<400> SEQUENCE: 2

Met Lys Lys Thr Ala Ile Ala Ile Ala Val Ala Leu Ala Gly Phe Ala
1               5                   10                  15

Thr Val Ala Gln Ala
            20
```

```
<210> SEQ ID NO 3
<211> LENGTH: 21
<212> TYPE: PRT
<213> ORGANISM: E. coli

<400> SEQUENCE: 3

Met Lys Gln Ser Thr Ile Ala Leu Ala Leu Leu Pro Leu Leu Phe Thr
1               5                   10                  15

Pro Val Thr Lys Ala
            20

<210> SEQ ID NO 4
<211> LENGTH: 25
<212> TYPE: PRT
<213> ORGANISM: E. coli

<400> SEQUENCE: 4

Met Met Ile Thr Leu Arg Lys Leu Pro Leu Ala Val Ala Val Ala Ala
1               5                   10                  15

Gly Val Met Ser Ala Gln Ala Met Ala
            20                  25

<210> SEQ ID NO 5
<211> LENGTH: 23
<212> TYPE: PRT
<213> ORGANISM: E. coli

<400> SEQUENCE: 5

Met Asn Lys Lys Val Leu Thr Leu Ser Ala Val Met Ala Ser Met Leu
1               5                   10                  15

Phe Gly Ala Ala Ala His Ala
            20

<210> SEQ ID NO 6
<211> LENGTH: 22
<212> TYPE: PRT
<213> ORGANISM: E. caratovora

<400> SEQUENCE: 6

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 7
<211> LENGTH: 23
<212> TYPE: PRT
<213> ORGANISM: E. coli

<400> SEQUENCE: 7

Met Lys Lys Asn Ile Ala Phe Leu Leu Ala Ser Met Phe Val Phe Ser
1               5                   10                  15

Ile Ala Thr Asn Ala Tyr Ala
            20

<210> SEQ ID NO 8
<211> LENGTH: 19
<212> TYPE: PRT
<213> ORGANISM: E. coli

<400> SEQUENCE: 8

Met Lys Lys Ile Trp Leu Ala Leu Ala Gly Leu Val Leu Ala Phe Ser
1               5                   10                  15
```

Ala Ser Ala

<210> SEQ ID NO 9
<211> LENGTH: 23
<212> TYPE: PRT
<213> ORGANISM: E. coli

<400> SEQUENCE: 9

Met Met Thr Lys Ile Lys Leu Leu Met Leu Ile Ile Phe Tyr Leu Ile
1               5                   10                  15

Ile Ser Ala Ser Ala His Ala
            20

<210> SEQ ID NO 10
<211> LENGTH: 21
<212> TYPE: PRT
<213> ORGANISM: E. coli

<400> SEQUENCE: 10

Met Lys Gln Ala Leu Arg Val Ala Phe Gly Phe Leu Ile Leu Trp Ala
1               5                   10                  15

Ser Val Leu His Ala
            20

<210> SEQ ID NO 11
<211> LENGTH: 18
<212> TYPE: PRT
<213> ORGANISM: E. coli

<400> SEQUENCE: 11

Met Arg Val Leu Leu Phe Leu Leu Leu Ser Leu Phe Met Leu Pro Ala
1               5                   10                  15

Phe Ser

<210> SEQ ID NO 12
<211> LENGTH: 7
<212> TYPE: PRT
<213> ORGANISM: Artificial Sequence
<220> FEATURE:
<223> OTHER INFORMATION: protease cleavage site within TEV NIa protein

<400> SEQUENCE: 12

Glu Asn Leu Tyr Phe Gln Gly
1               5

<210> SEQ ID NO 13
<211> LENGTH: 8
<212> TYPE: PRT
<213> ORGANISM: Artificial Sequence
<220> FEATURE:
<223> OTHER INFORMATION: protease cleavage site within HRV 3C protein

<400> SEQUENCE: 13

Leu Glu Val Leu Phe Gln Gly Pro
1               5

<210> SEQ ID NO 14
<211> LENGTH: 5
<212> TYPE: PRT
<213> ORGANISM: Artificial Sequence
<220> FEATURE:
<223> OTHER INFORMATION: protease cleavage site within Enterokinase
      protein

<400> SEQUENCE: 14

Asp Asp Asp Asp Lys
1               5

<210> SEQ ID NO 15
<211> LENGTH: 4
<212> TYPE: PRT
<213> ORGANISM: Artificial Sequence
<220> FEATURE:
<223> OTHER INFORMATION: protease cleavage site within Fator Xa protein

<400> SEQUENCE: 15

Ile Glu Gly Arg
1

<210> SEQ ID NO 16
<211> LENGTH: 5
<212> TYPE: PRT
<213> ORGANISM: Artificial Sequence
<220> FEATURE:
<223> OTHER INFORMATION: protease cleavage site within Thrombin (fIIa)
      protein

<400> SEQUENCE: 16

Leu Val Pro Arg Gly
1               5

<210> SEQ ID NO 17
<211> LENGTH: 57
<212> TYPE: DNA
<213> ORGANISM: E. coli

<400> SEQUENCE: 17
atgaaaaaga tttggctggc gctggctggt ttagttttag cgtttagcgc atcggcg       57

<210> SEQ ID NO 18
<211> LENGTH: 63
<212> TYPE: DNA
<213> ORGANISM: E. coli

<400> SEQUENCE: 18
atgaaaaaaa cggcaattgc gatagcggtt gcgctagctg gttttgccac ggtggcgcag    60
gct                                                                 63

<210> SEQ ID NO 19
<211> LENGTH: 78
<212> TYPE: DNA
<213> ORGANISM: E. coli

<400> SEQUENCE: 19
atgaaaataa aaacaggtgc acgcatcctc gcattatccg cattaacgac gatgatgttt    60
tccgcctcgg ctctcgcc                                                 78

<210> SEQ ID NO 20
<211> LENGTH: 7
<212> TYPE: PRT
<213> ORGANISM: Artificial Sequence
<220> FEATURE:
<223> OTHER INFORMATION: tobacco etch virus protease
<220> FEATURE:
<221> NAME/KEY: misc_feature
<222> LOCATION: (7)..(7)
<223> OTHER INFORMATION: Xaa can be Gly or Ser

<400> SEQUENCE: 20

```
Glu Asn Leu Tyr Phe Gln Xaa
1               5

<210> SEQ ID NO 21
<211> LENGTH: 5
<212> TYPE: PRT
<213> ORGANISM: Artificial Sequence
<220> FEATURE:
<223> OTHER INFORMATION: yellow fever virus protease
<220> FEATURE:
<221> NAME/KEY: misc_feature
<222> LOCATION: (5)..(5)
<223> OTHER INFORMATION: Xaa can be Gly or Ser

<400> SEQUENCE: 21

Gly Ala Arg Arg Xaa
1               5

<210> SEQ ID NO 22
<211> LENGTH: 6
<212> TYPE: PRT
<213> ORGANISM: Artificial Sequence
<220> FEATURE:
<223> OTHER INFORMATION: thrombin

<400> SEQUENCE: 22

Leu Val Pro Arg Gly Ser
1               5

<210> SEQ ID NO 23
<211> LENGTH: 4
<212> TYPE: PRT
<213> ORGANISM: Artificial Sequence
<220> FEATURE:
<223> OTHER INFORMATION: Factor Xa
<220> FEATURE:
<221> NAME/KEY: misc_feature
<222> LOCATION: (2)..(2)
<223> OTHER INFORMATION: Xaa can be Glu or Asp

<400> SEQUENCE: 23

Ile Xaa Gly Arg
1

<210> SEQ ID NO 24
<211> LENGTH: 7
<212> TYPE: PRT
<213> ORGANISM: Artificial Sequence
<220> FEATURE:
<223> OTHER INFORMATION: SV40 large T-cell antigen peptide

<400> SEQUENCE: 24

Pro Lys Lys Lys Arg Lys Val
1               5

<210> SEQ ID NO 25
<211> LENGTH: 16
<212> TYPE: PRT
<213> ORGANISM: Artificial Sequence
<220> FEATURE:
<223> OTHER INFORMATION: nucleoplasmin peptide

<400> SEQUENCE: 25

Lys Arg Pro Ala Ala Thr Lys Lys Ala Gly Gln Ala Lys Lys Lys Lys
1               5                   10                  15

<210> SEQ ID NO 26
```

```
<211> LENGTH: 5
<212> TYPE: PRT
<213> ORGANISM: Artificial Sequence
<220> FEATURE:
<223> OTHER INFORMATION: enterokinase cleavage site

<400> SEQUENCE: 26

Asp Asp Asp Asp Lys
1               5
```